(12) United States Patent
Cruise et al.

(10) Patent No.: US 6,371,975 B2
(45) Date of Patent: Apr. 16, 2002

(54) COMPOSITIONS, SYSTEMS, AND METHODS FOR CREATING IN SITU, CHEMICALLY CROSS-LINKED, MECHANICAL BARRIERS

(75) Inventors: Gregory M Cruise, Fremont; Olexander Hnojewyj, Saratoga, both of CA (US)

(73) Assignee: NeoMend, Inc., Sunnyvale, CA (US)

( * ) Notice: Subject to any disclaimer, the term of this patent is extended or adjusted under 35 U.S.C. 154(b) by 0 days.

(21) Appl. No.: 09/188,083

(22) Filed: Nov. 6, 1998

(51) Int. Cl.$^7$ ................................................ A61B 17/08
(52) U.S. Cl. ................................................ 606/214
(58) Field of Search ................................ 606/213, 214, 606/216; 424/426, 489, 490; 528/354, 355, 357, 361; 525/54.1, 54.2, 408, 415; 128/898

(56) References Cited

U.S. PATENT DOCUMENTS

| | | |
|---|---|---|
| 4,101,380 A | 7/1978 | Rubinstein et al. |
| 4,161,948 A | 7/1979 | Bichon |
| 4,464,468 A | 8/1984 | Avrameas et al. |
| 4,839,345 A | 6/1989 | Doi et al. |

(List continued on next page.)

FOREIGN PATENT DOCUMENTS

| | | |
|---|---|---|
| WO | WO 96/11671 | 10/1994 |
| WO | WO 97/22371 | 6/1997 |
| WO | WO 99/07417 | 8/1997 |
| WO | WO 99/14259 | 9/1997 |
| WO | WO 99/45964 | 3/1998 |
| WO | WO 00/09087 | 8/1998 |
| WO | WO 00/09199 | 8/1998 |
| WO | WO 00/33764 | 12/1998 |

OTHER PUBLICATIONS

Transactors: Society for Biomaterials: "Protoelytically Degradable Hydrogels": West et al (1997) Tab L.

*Primary Examiner*—Olik Chaudhuri
*Assistant Examiner*—(Vikki) Hoa B. Trinh
(74) *Attorney, Agent, or Firm*—Ryan Kromholz & Manion

(57) ABSTRACT

A biocompatible and biodegradable barrier material is applied to a tissue region, e.g., to seal a vascular puncture site. The barrier material comprises a compound, which is chemically cross-linked without use of an enzyme to form a non-liquid mechanical matrix. The compound preferably includes a protein comprising recombinant or natural serum albumin, which is mixed with a polymer that comprises poly(ethylene) glycol (PEG), and, most preferably, a multi-armed PEG polymer.

9 Claims, 22 Drawing Sheets

U.S. PATENT DOCUMENTS

| | | |
|---|---|---|
| 5,051,406 A | 9/1991 | Satoh |
| 5,129,882 A | 7/1992 | Welden et al. |
| 5,207,670 A | 5/1993 | Sinofsky |
| 5,252,714 A | 10/1993 | Harris et al. |
| 5,318,524 A | 6/1994 | Morse et al. |
| 5,529,577 A | 7/1994 | Hammerslag |
| 5,383,896 A | 1/1995 | Gershony et al. |
| 5,403,278 A | 4/1995 | Ernst et al. |
| 5,410,016 A | 4/1995 | Hubbell et al. |
| 5,419,765 A | 5/1995 | Weldon et al. |
| 5,514,379 A | 5/1996 | Weissleder et al. |
| 5,520,885 A | 5/1996 | Coelho et al. |
| 5,567,435 A | 10/1996 | Hubbell et al. |
| 5,583,114 A | 12/1996 | Barrows et al. |
| 5,601,602 A | 2/1997 | Fowler |
| 5,626,601 A | 5/1997 | Gershony et al. |
| 5,626,863 A | 5/1997 | Hubbell et al. |
| 5,653,730 A | 8/1997 | Hammeslag |
| 5,672,662 A | 9/1997 | Harris et al. |
| 5,676,689 A | 10/1997 | Kensey et al. |
| 5,725,498 A | 3/1998 | Janzen et al. |
| 5,733,563 A | 3/1998 | Fortier |
| 5,739,208 A | 4/1998 | Harris |
| 5,759,194 A | 6/1998 | Hamerslag |
| 5,782,860 A | 7/1998 | Epstein et al. |
| 5,791,352 A | 8/1998 | Reich et al. |
| 5,824,015 A | 10/1998 | Sawyer |
| 5,843,124 A | 12/1998 | Hammerslag |
| 5,844,016 A | 12/1998 | Sawhney et al. |
| 5,858,746 A | 1/1999 | Hubbell et al. |
| 5,874,500 A | 2/1999 | Rhee et al. |
| 5,900,245 A | 5/1999 | Sawhney et al. |
| 5,900,461 A | 5/1999 | Harris |
| 5,922,009 A | 7/1999 | Epstein et al. |
| 5,932,462 A | 8/1999 | Harris et al. |
| 5,935,147 A | 8/1999 | Kensey et al. |
| 5,936,035 A | 8/1999 | Rhee et al. |
| 5,942,209 A | 8/1999 | Leavitt et al. |
| 5,951,583 A | 9/1999 | Jensen et al. |
| 5,951,589 A | 9/1999 | Epstein et al. |
| 5,986,043 A | 11/1999 | Hubbell et al. |
| 5,990,237 A | 11/1999 | Bentley et al. |
| 6,007,613 A | 12/1999 | Izoret |
| 6,022,361 A | 2/2000 | Epstein et al. |
| 6,051,248 A * | 4/2000 | Sawhney et al. ........... 424/426 |
| 6,060,582 A * | 5/2000 | Hubbell et al. ............. 528/354 |
| 6,083,524 A | 7/2000 | Sawhney et al. |
| 6,152,943 A | 11/2000 | Sawhney |
| 6,162,241 A | 12/2000 | Coury et al. |
| 6,165,201 A | 12/2000 | Sawhney et al. |
| 6,177,095 B1 | 1/2001 | Sawhney et al. |
| 6,179,862 B1 | 1/2001 | Sawhney |

* cited by examiner

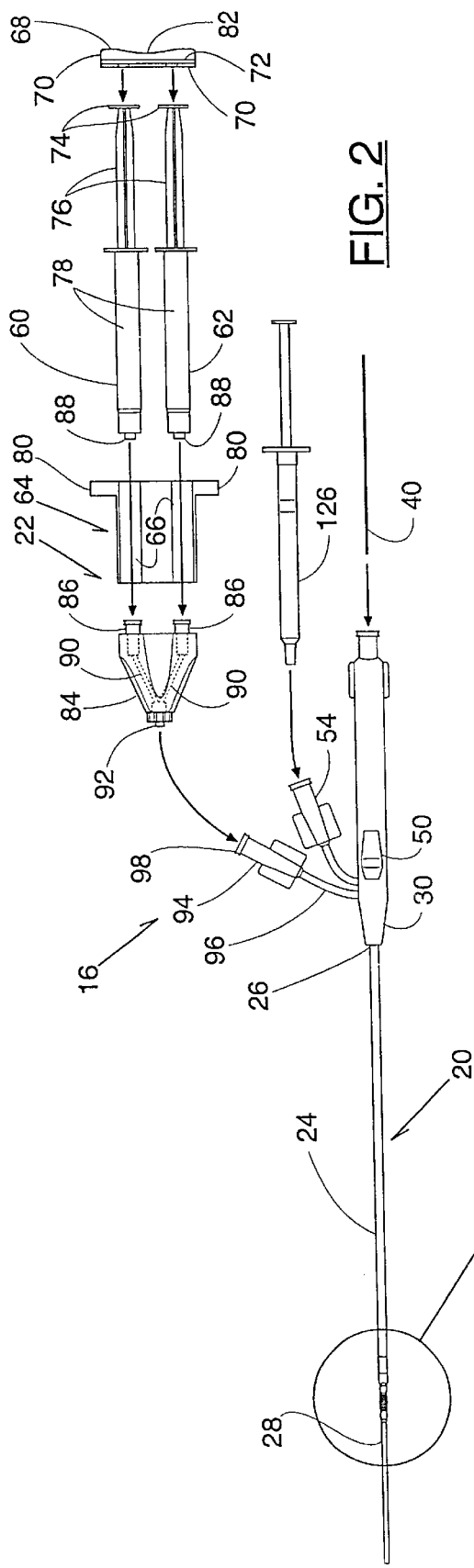
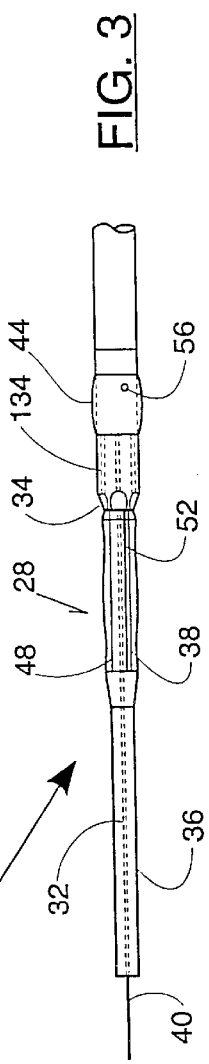
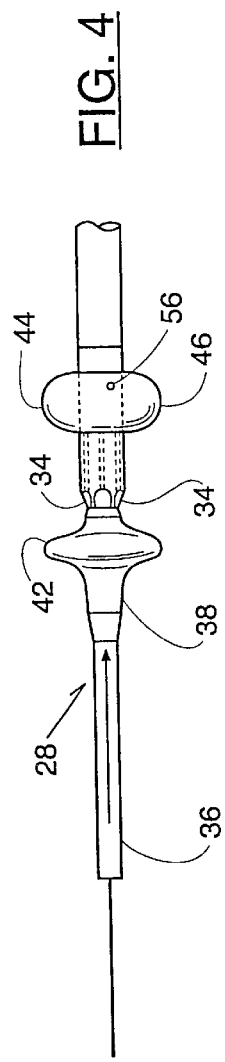
FIG. 2
FIG. 3
FIG. 4

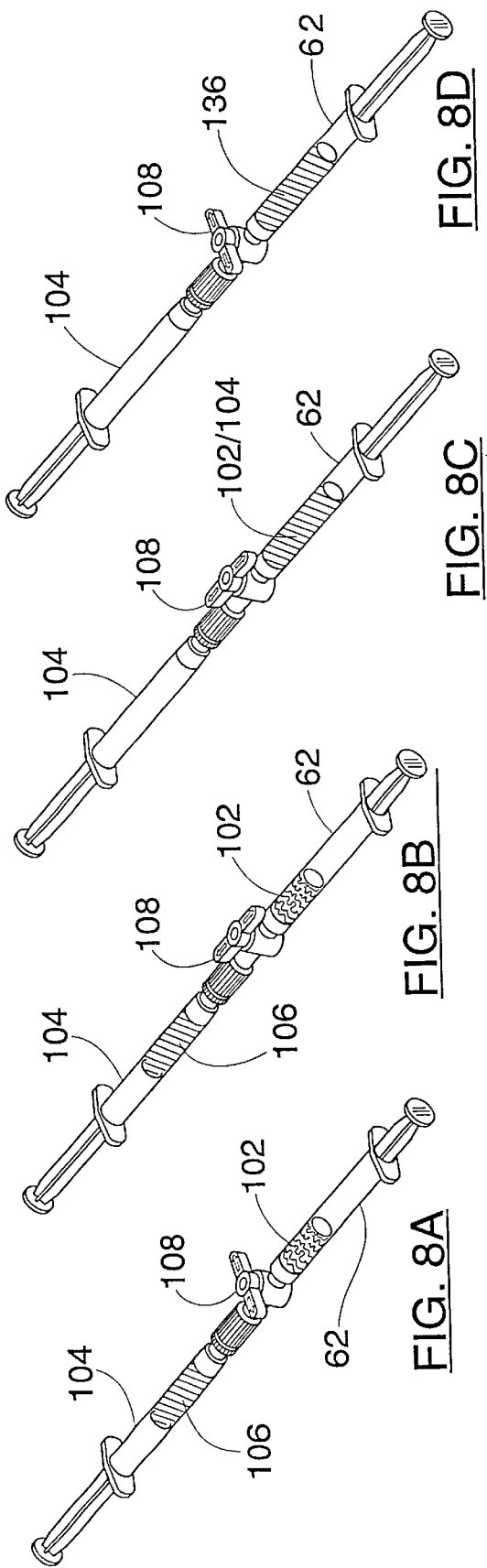

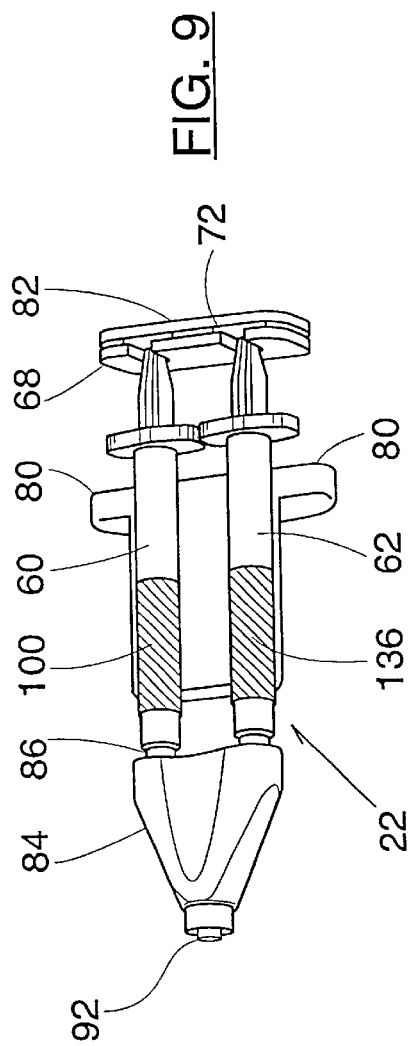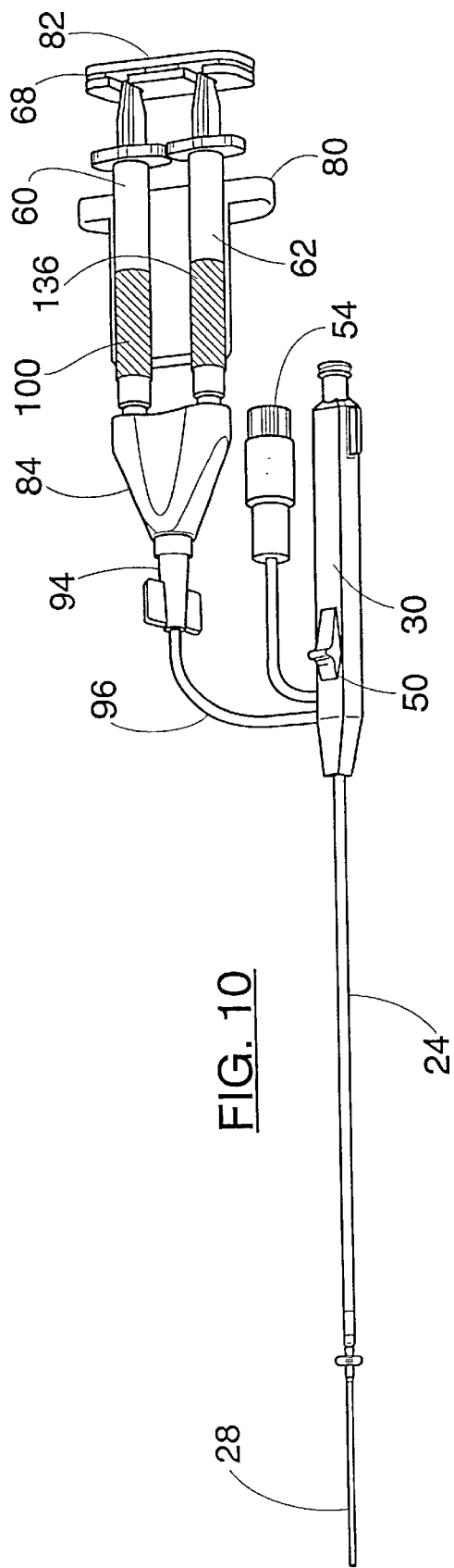
FIG. 9
FIG. 10

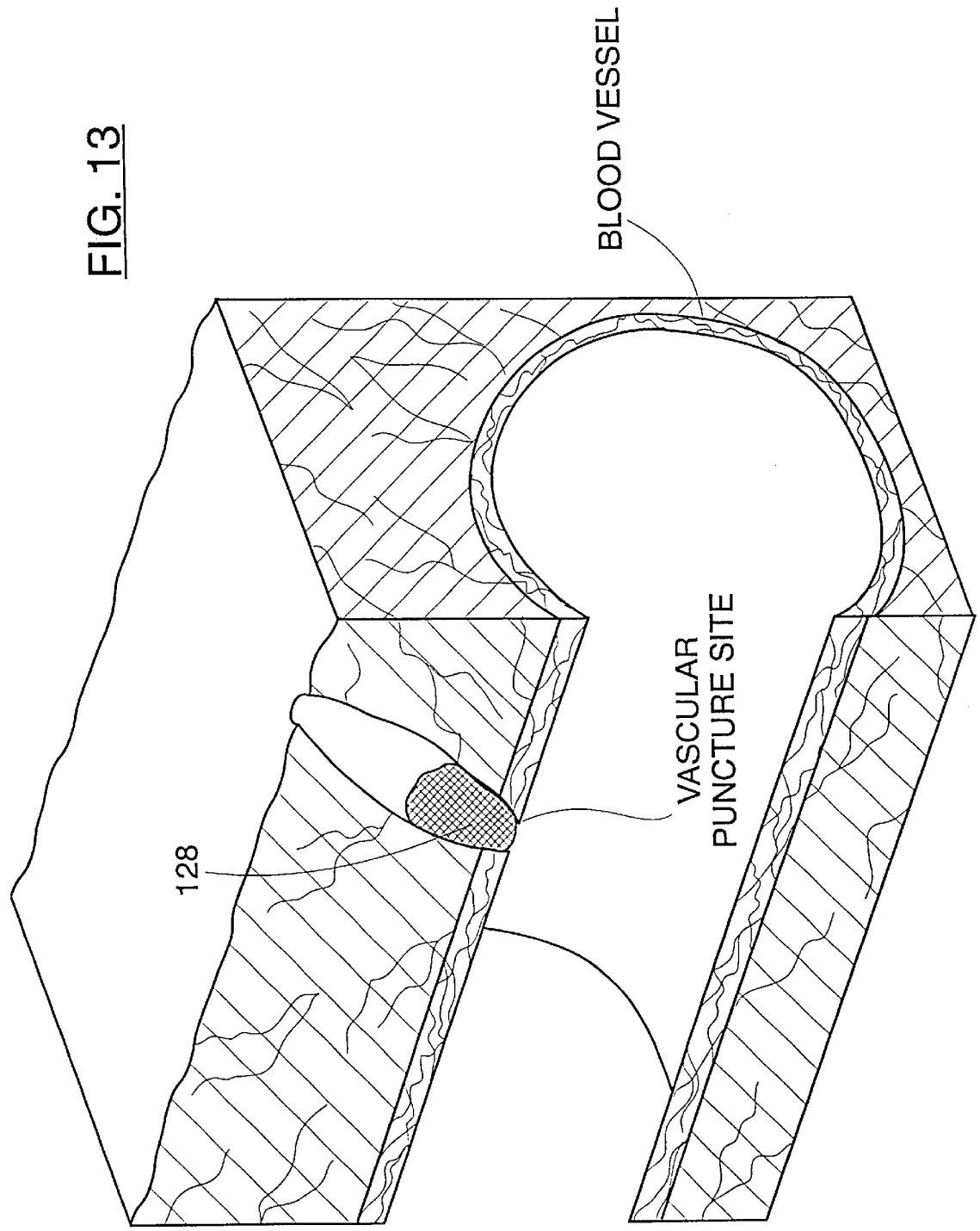

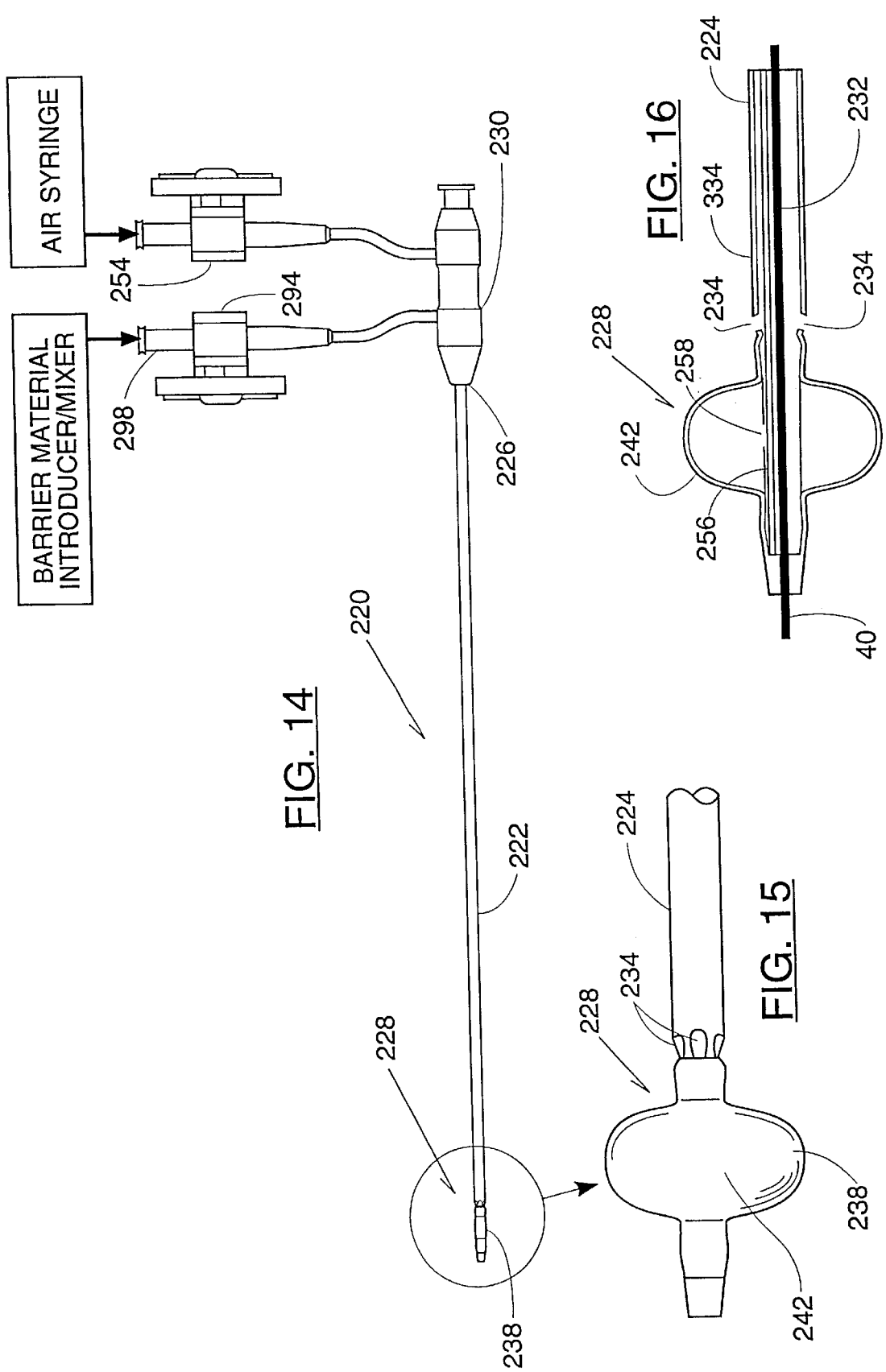

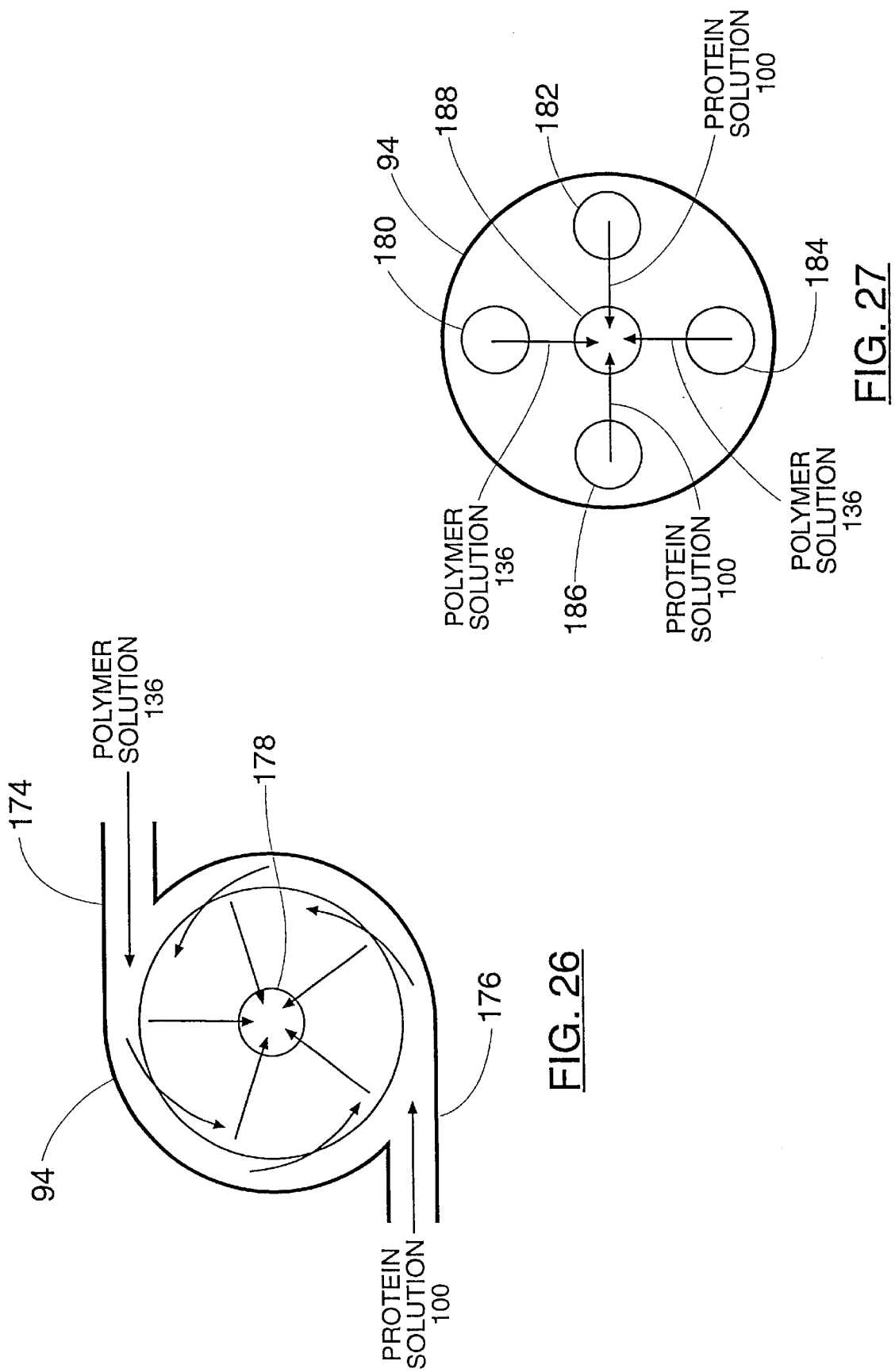

COMPOSITIONS, SYSTEMS, AND METHODS FOR CREATING IN SITU, CHEMICALLY CROSS-LINKED, MECHANICAL BARRIERS

FIELD OF THE INVENTION

The invention generally relates to the formation and application of barrier materials in a tissue region, e.g., to close vascular puncture sites in humans and other animals.

BACKGROUND OF THE INVENTION

There are over seven million diagnostic and therapeutic coronary interventions performed each year. By far, the majority of these interventions are performed using percutaneous puncture of the femoral artery to gain access to the arterial system.

Once the intervention is concluded, the vascular puncture site has to be sealed to prevent bleeding, while natural healing processes close the puncture site. Conventional management of the puncture site has typically involved external compression using, e.g., digital pressure, C-clamps, or sandbags, followed by immobilization and bedrest. Proper placement of compression devices to stop bleeding calls for trained clinical skills. Likewise, strong nursing skills are required to monitor for rebleeding. The patient can suffer local discomfort, which may exceed the pain associated with the diagnostic or therapeutic procedure requiring vascular access in the first instance. Complications are not uncommon, which can lead to prolonged hospitalization, transfusion, and direct surgical repair of the puncture site.

Various alternative methods for sealing a vascular puncture site have been tried. For example, collagen plugs have been used to occlude the puncture orifice. The collagen plugs are intended to activate platelets and accelerate the natural healing process. Holding the collagen seals in place using an anchor located inside the artery has also been tried. Still, patient immobilization is required until clot formation stabilizes the site. Other problems, such as distal embolization of the collagen, rebleeding, and the need for external pressure to achieve hemostatis, also persist.

As another example, devices that surgically suture the puncture site percutaneously have also been used. The devices require the practice of fine surgical skills to place four needles at a precise distance from the edges of the puncture orifice and to form an array of suture knots, which are tightened, resulting in puncture edge apposition.

There remains a need for fast and straightforward mechanical and chemical systems and methods to close vascular puncture sites and to accelerate the patient's return to ambulatory status without pain and prolonged immobilization.

SUMMARY OF THE INVENTION

The invention provides compositions, instruments, systems, and methods, which, in use, produce fast and effective closure to vascular puncture sites, and which allow a patient to return to ambulatory status quickly following a vascular access procedure.

One aspect of the invention a biocompatible and biodegradable barrier material, which is applied to seal a vascular puncture site. The barrier material comprises a compound, which is chemically cross-linked without use of an enzyme to form a non-liquid mechanical matrix.

In a preferred embodiment, the compound includes a protein comprising recombinant or natural serum albumin. In this embodiment, the compound also includes a polymer that comprises a poly(ethylene) glycol (PEG). Most preferably, the the PEG comprises a multi-armed polymer.

In a preferred embodiment, the barrier material, applied to seal a vascular puncture site, comprises a mixture of a first liquid component and a second liquid component, which are chemically cross-linked, without use of an enzyme, to form a non-liquid mechanical matrix.

This aspect of the invention also provides a kit comprising a first dispenser containing a first liquid component a second dispenser containing a second liquid component.

The kit includes instructions for handling the first and second dispensers according to a method comprising the steps of mixing the first and second liquid components to chemically cross-link the first and second components, without use of an enzyme, to form a non-liquid mechanical matrix, and applying the mechanical matrix to seal a vascular puncture site.

This aspect of the invention provides a chemically cross-linked barrier material that is not formed through the use of enzymes. Reliance upon enzymes as cross-linking agents can pose problems with regard to availability, cost, and possible viral transmission. The invention obviates these problems.

Another aspect of the invention provides a barrier material comprising a protein portion and polymer portion forming a cross-linked, hydrogel network. The barrier material is nontoxic, biodegradable, and possesses the mechanical properties necessary to seal arterial pressure.

In a preferred embodiment, the protein portion of the barrier material is a biocompatible, readily available, water soluble protein, such as a serum protein like albumin. The protein solution is preferably buffered to a pH in the range of 7.0 to 10.0.

In a preferred embodiment, the polymer portion of the barrier material is an electrophilic derivative of a hydrophilic polymer with a functionality of at least three. The preferred electrophilic group is an N-hydroxysuccinimide ester, due to its speed of reaction and low toxicity.

In a preferred embodiment, the polymer includes a region that controls degradation to impart biodegradation or non-biodegradation to the barrier material. The most preferred polymer for degradable barrier materials is poly(ethylene glycol) tetra-succinimidyl glutarate, however a number different polymers, electrophilic derivatives, and degradation control regions can be utilized.

Upon mixing, the polymer solution reacts with the protein solution, forming a cross-linked network in a prescribed amount of time. The rate of cross-linking can be controlled by the buffer in the protein solution. The mechanical properties of the barrier material can be controlled by the polymeric nature, structure, and concentration in the reactive mixture. The electrophilic derivative of the hydrophilic polymer not only reacts with the protein solution, but also reacts with the surrounding tissue in the site of application, creating an anchor for the material.

After the barrier material is formed, the degradation of the barrier material is controlled by the selection of the degradation control region. If degradation is desired, a degradation control region is selected that is able to be hydrolytically or enzymatically degraded in a physiological environment. The degrading molecules of the hydrogel barrier matrix are cleared through the kidneys and eliminated in the urine. If degradation is not desired, a degradation control region is selected that is stable in a physiological environment.

Another aspect of the invention provides systems and methods for creating and applying a biocompatible barrier in a tissue region. The systems and methods mix a protein solution and a polymer solution including a derivative of a hydrophilic polymer with a functionality of at least three. Upon mixing, the protein solution and the polymer solution cross-link to form a mechanical non-liquid matrix.

In a preferred embodiment, the systems and methods apply the barrier material to seal a vascular puncture site.

Features and advantages of the inventions are set forth in the following Description and Drawings, as well as in the appended Claims.

BRIEF DESCRIPTION OF THE DRAWINGS

FIG. 2 is an exploded plan view of the contents of the site access kit and barrier component kit shown in FIG. 1, illustrating their assembly for use;

FIG. 3 is an enlarged view of the distal end of the catheter tube of a catheter device contained in the site access kit shown in FIG. 1, showing two deformable regions in a relaxed condition for deployment to a vascular puncture site;

FIG. 4 is an enlarged view of the distal end of the catheter tube shown in FIG. 3, illustrating two deformable regions in an enlarged condition, ready for use at the vascular puncture site;

FIGS. 8A to 8D are perspective views showing the manipulation of syringes contained in the barrier component kit shown in FIG. 7B, to create a liquid PEG solution for use with the system;

FIG. 9 is a perspective view of the barrier material introducer/mixer contained in the site access kit shown in FIG. 1, with the syringes containing the liquid albumin solution and the liquid PEG solution (mixed as shown in FIGS. 8A to 8D) mounted and ready for use;

FIG. 10 is a perspective view of the barrier material introducer/mixer shown in FIG. 9 attached for operation with the catheter device contained in the site access kit shown in FIG. 1;

FIG. 13 is a schematic, perspective view of the vascular puncture site shown in FIG. 12, with the non-liquid barrier network remaining in the tissue region outside the puncture site, to seal the puncture site, after withdrawal of the catheter device;

FIG. 14 is a plan view of an alternative embodiment of a catheter device which can be used in association with the system shown in FIG. 1, with the deformable region on the distal end shown in a collapsed condition;

FIG. 15 is an enlarged view of the distal end of the catheter device shown in FIG. 14, with the deformable region in an expanded condition;

FIG. 16 is an enlarged sectional view of the distal end of the catheter device shown in FIG. 15;

FIG. 26 is an enlarged sectional view showing the interior of a mixing chamber usable in association with the barrier material introducer shown in FIG. 9, the interior establishing tangential flow paths within through the chamber for the purpose of accelerating mixing of the liquid components of the barrier material;

FIG. 27 is an enlarged sectional view showing the interior of a mixing chamber usable in association with the barrier material introducer shown in FIG. 9, the interior containing multiple, independent inlet ports to convey liquid components into the chamber for the purpose of accelerating mixing of the liquid components of the barrier material;

The invention may be embodied in several forms without departing from its spirit or essential characteristics. The scope of the invention is defined in the appended claims, rather than in the specific description preceding them. All embodiments that fall within the meaning and range of equivalency of the claims are therefore intended to be embraced by the claims.

DETAILED DESCRIPTION OF THE PREFERRED EMBODIMENTS

Figure 1:
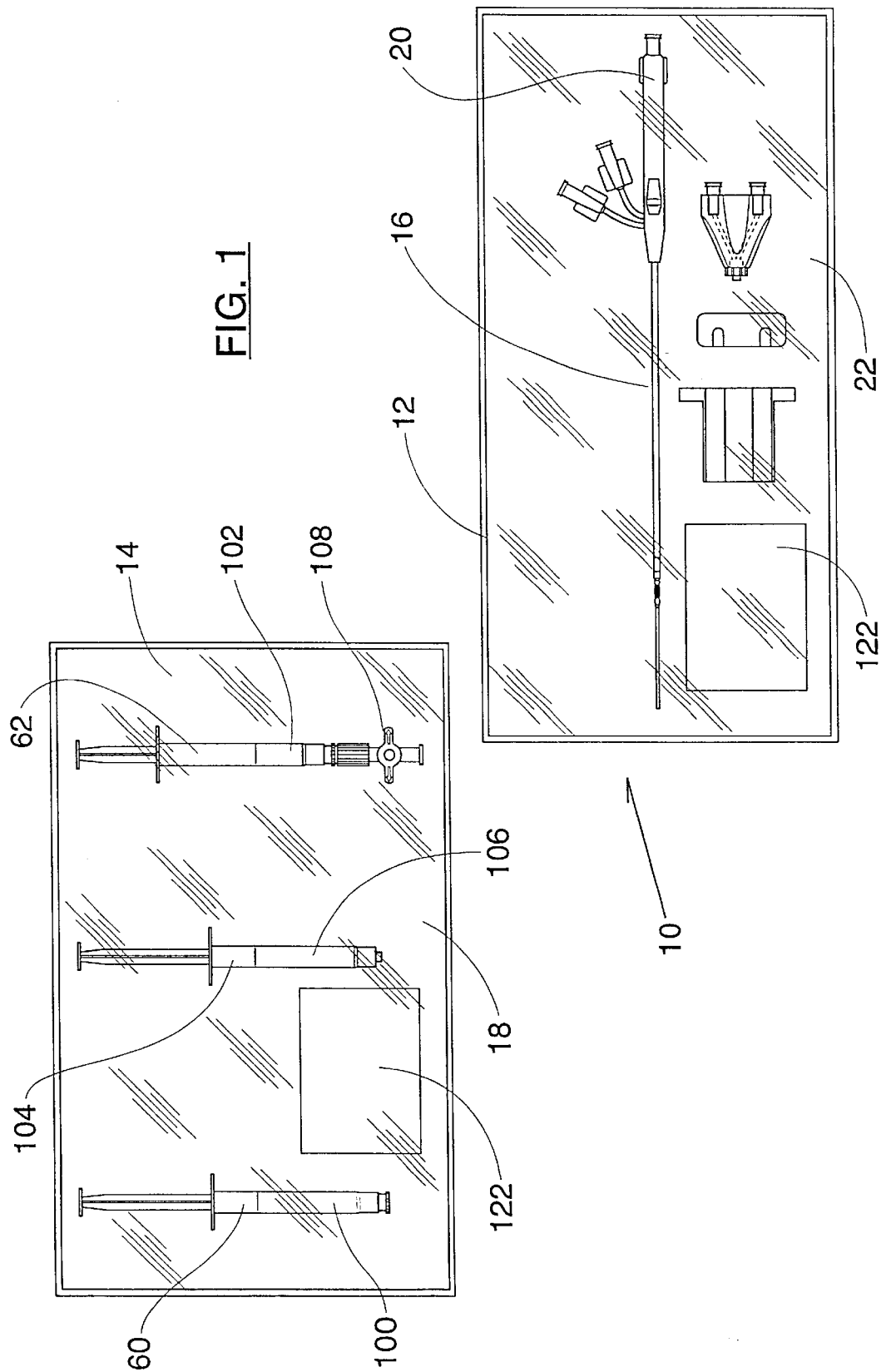
FIG. 1 is a plan view of a system for creating a mechanical barrier to seal a vascular puncture site, showing the components of the system prepackaged in a site access kit and a barrier component kit.

FIG. 1 shows a system 10 of functional instruments for sealing a vascular puncture site. As will be described in greater detail, the instruments of the system 10 are, during use, deployed in a purposeful manner to gain subcutaneous access to a vascular puncture site. At the site, the instruments of the system 10 are manipulated to introduce an inert barrier material in liquid form outside the blood vessel at the puncture site. The material quickly transforms into a non-liquid structure in situ, forming a barrier outside the vessel, which mechanically seals the puncture. The barrier exists long enough to prevent blood leakage while natural healing processes close the puncture site. The barrier is, over time, degraded by hydrolysis by in the host body and cleared by the kidneys in the urine.

As FIG. 1 shows, in the illustrated embodiment, the system 10 is consolidated in two functional kits 12 and 14.

The first kit 14 contains a vascular puncture site access assembly 16. The purpose of the access assembly 16 is to gain subcutaneous access to the vascular puncture site for the purpose of delivering the fluid barrier material.

The second kit 14 contains a barrier component assembly 18. The purpose of the barrier component assembly 18 is to house the components of the fluid barrier material prior to use. As will be described in greater detail later, these components are mixed and delivered by the access assembly 16 to the puncture site, forming the barrier.

The kits 12 and 14 can take various forms. In the illustrated embodiment, each kit 12 and 14 comprises a sterile, wrapped assembly, the details of which will be discussed in greater detail later.

I. The Access Assembly

As FIG. 2 shows, the access assembly 16 comprises a catheter device 20 and a barrier material introducer/mixer 22.

A. The Catheter Device

The catheter device 20 includes a flexible catheter tube 24 having a proximal end 26 and a distal end 28. The catheter tube 24 can be constructed, for example, using standard flexible, medical grade plastic materials, like vinyl, nylon, poly(ethylene), ionomer, poly(urethane), poly(amide), and poly(ethylene terephthalate). The distal end 28 has an outside diameter of, e.g., 4 Fr to 16 Fr. The proximal end 26 carries a handle 30 to facilitate gripping and maneuvering the catheter tube 24 by a physician.

As FIG. 3 shows, an interior lumen 32 extends through the catheter tube 24. The lumen accommodates passage of a conventional guide wire 40.

Figure 5:
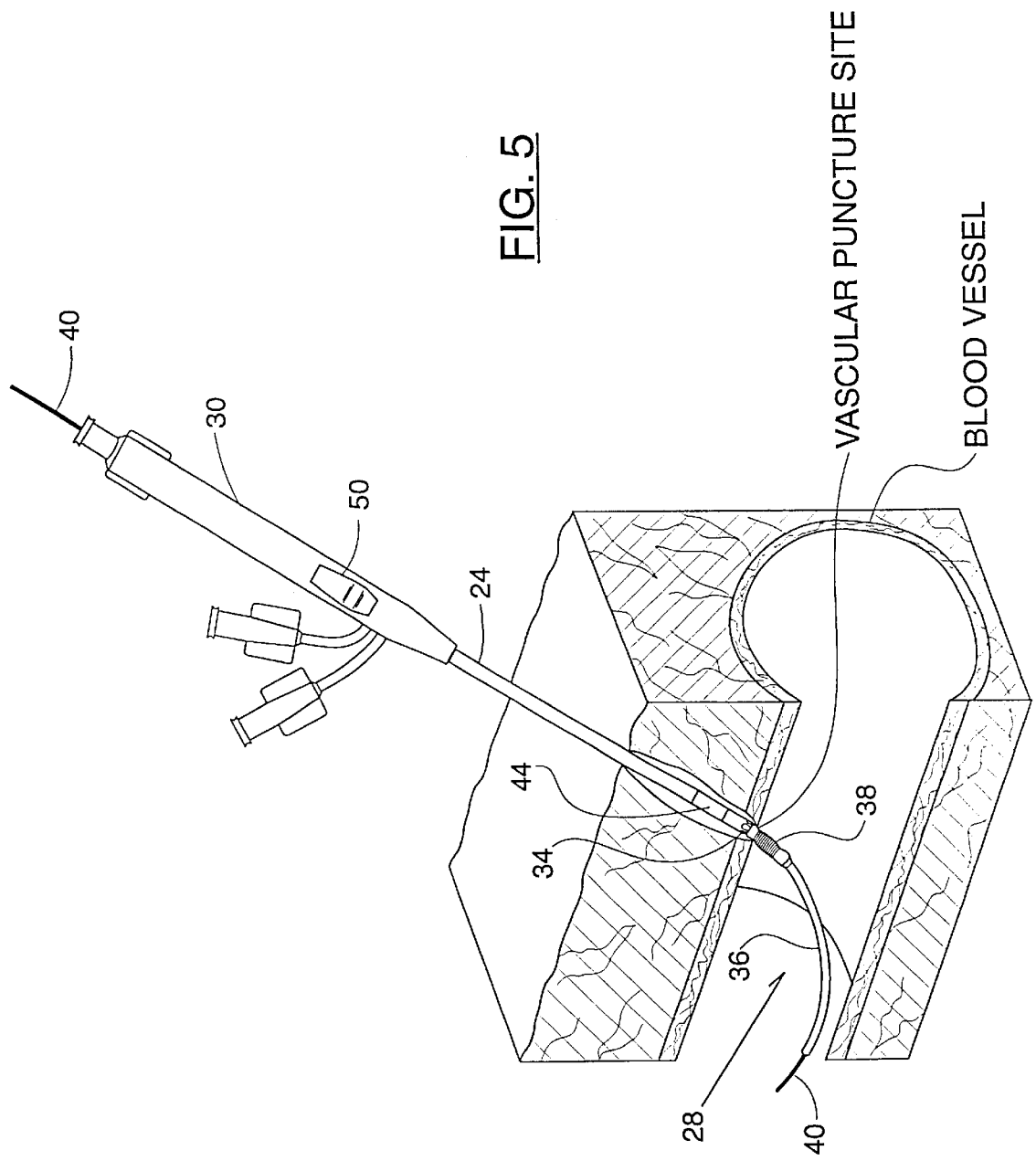
FIG. 5 is a schematic perspective view of the distal catheter end in the relaxed condition shown in FIG. 3, when deployed at a vascular puncture site.

As will be described in greater detail later, the guide wire 40 typically will have been previously introduced subcutaneously, through a wall of the vessel, to guide passage of a desired therapeutic or diagnostic instrument into the vessel, e.g., to perform coronary angioplasty. After performing the intended procedure, the instrument is withdrawn, leaving the guide wire 40. As FIG. 5 shows, the distal end 28 of the catheter tube 24 is passed over the same guide wire 40 into the blood vessel. Manipulation of the distal end 28 closes the vascular puncture site and stops bleeding.

As FIGS. 3 and 4 show, the distal end 28 of the catheter tube 24 includes a circumferentially spaced array of nozzles 34. The barrier material is conveyed in liquid form and dispensed in a circumferential manner through the nozzles 34 at the puncture site.

As FIGS. 3 and 4 also show, the distal end 28 also includes a flexible, elongated leader 36, which extends distally beyond the nozzles 34. In use (see FIG. 5), the leader 36 is located inside the blood vessel immediately interior to the puncture site. In use (see FIG. 5), the array of nozzles 34 is located outside the blood vessel immediately exterior to the puncture site.

Referring again to FIGS. 3 and 4, the distal end 28 also includes a first deformable region 38, which is located between the nozzles 34 and the leader 36. The region 38 normally presents a generally cylindrical, low profile condition (shown in FIG. 3), matching the leader 36. When in the low profile condition, the region 38 follows the leader 36 over the guide wire into the vessel (see FIG. 5).

Figure 6:
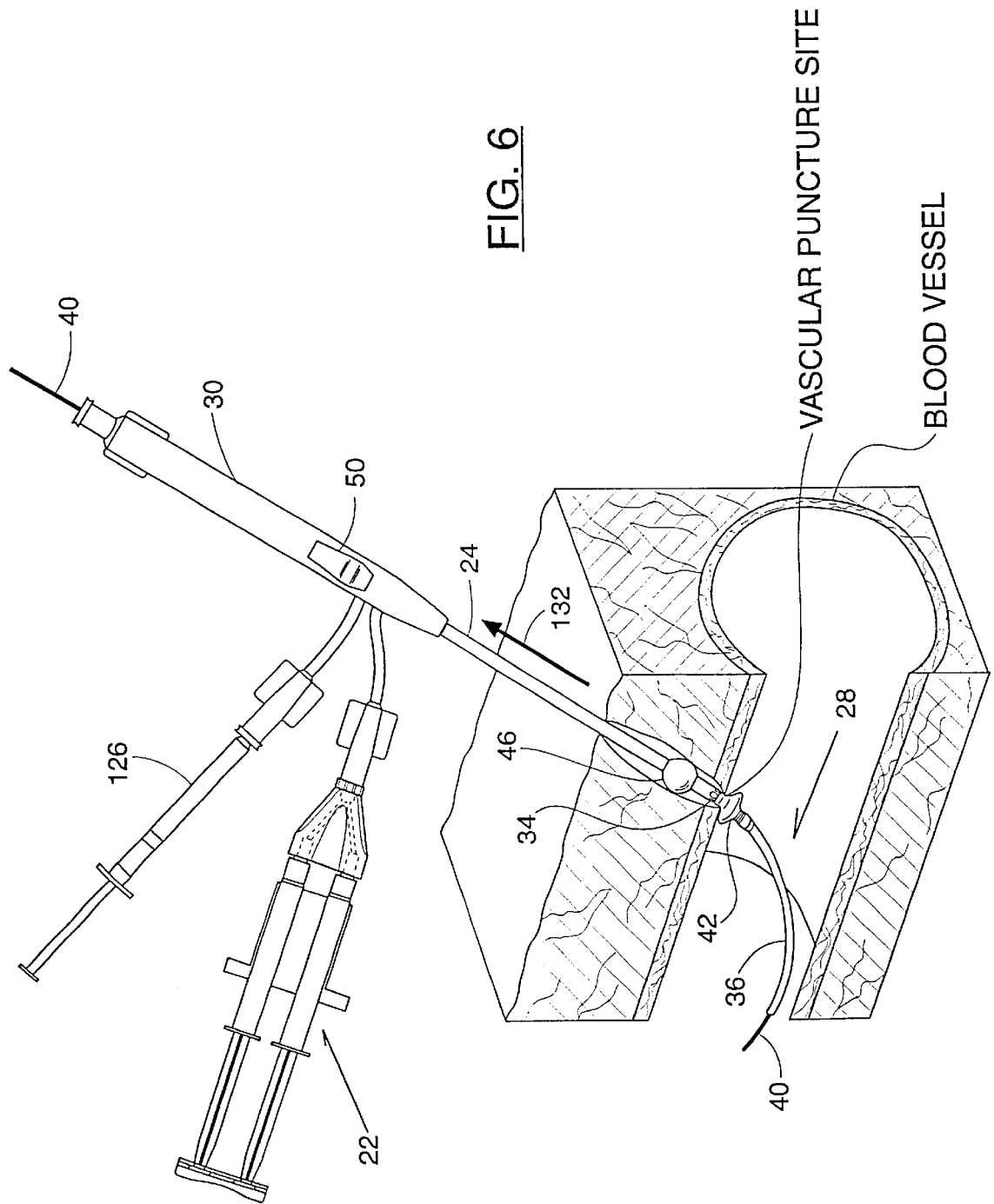
FIG. 6 is a schematic perspective view of the distal catheter end in the enlarged condition shown in FIG. 4, when deployed at a vascular puncture site.

The region 38 can be deformed into a radially enlarged condition, which forms a positioner 42 (see FIG. 4). In use (see FIG. 6), the positioner 42 resists passage of the leader 36 back through the puncture site in response to rearward tension along the catheter tube 24, as shown by arrow 132 in FIG. 6. Moreover, as FIG. 6 shows, rearward tension along the catheter tube 24 seats the positioner 42 against the interior of vessel wall at the puncture site. The positioner 42 serves to position the nozzles 34 at a proper distance outside the vessel. The positioner 42 also serves to support the puncture site inside the vessel while the liquid barrier material is introduced outside the vessel through the nozzles 34.

Referring back to FIGS. 3 and 4, a second deformable region 44 is spaced a distance proximal to the nozzles 34. Like the nozzles 34 (see FIG. 5), the deformable region 44 is intended, during use, to lay outside the vessel.

The deformable region 44 presents a normally, generally collapsed condition for deployment over the guide wire 40 (shown in FIGS. 3 and 5). The deformable region 44 can be expanded into, e.g., an elliptical dam 46(see FIGS. 4 and 6). The dam 46 serves block proximal egress of the liquid barrier material conveyed through the nozzles 34.

The deformation of the regions 38 and 44 can be accomplished in various ways. In the illustrated embodiment, the leader 36 moves along a slide tube 48 (see FIGS. 3 and 4) toward and away from the nozzles 34. A push-pull lever 50 on the handle 30 (shown in FIG. 2) is coupled by a stylet 52 to the leader 36 to affect axial movement of the leader 36 along the slide tube 48.

In this arrangement, the region 38 comprises a generally elastic material surrounding the slide tube 48. The material is attached at one end to the leader 36 and at the other end to the catheter tube 24 near the nozzles 34. Drawing the leader 36 toward the nozzles 34 pushes against and radially deforms the material into the positioner 42. Advancement of the leader 36 away from the nozzles 34 relaxes the material.

In the illustrated embodiment, the second region 44 comprises an expandable balloon material attached about the catheter tube 24. The catheter tube 24 includes an interior lumen 56 (shown in FIGS. 3 and 4), which communicates with the interior of the balloon material. A fitting 54 carried by the handle 30 (see FIG. 2) communicates with the lumen 56. The fitting 54 couples the lumen to an auxiliary syringe 126, which injects air under pressure through the lumen 56 into the space surrounded by the balloon material, causing the material to expand and form the dam 46.

B. Barrier Material Introducer/Mixer

As will be described in greater detail later, the barrier material is formed from two liquid components, which are mixed at the instant of use. The two components cross-link to form the non-liquid barrier.

Before mixing, the components are housed in sterile dispensing syringes 60 and 62 contained in the kit 14 (see FIG. 1). As FIG. 2 shows, the barrier material introducer/mixer 22 receives the two dispensing syringes 60 and 62 for use in association with the catheter device 20. The barrier material introducer/mixer 22 allows the am physician to uniformly express the two components in a liquid state from the dispensing syringes 60 and 62.

The barrier material introducer/mixer 22 also mixes the components while flowing in the liquid state from the dispensing syringes 60 and 62. This obviates the need for static mixing prior to dispensing. This mixing of liquid components within a flow channel will, in shorthand, be called "channel-mixing."

To accomplish these functions (see FIG. 2), the barrier material introducer/mixer 22 includes syringe support 64. The support 64 includes side-by-side channels 66. Each channel 66 accommodates in a snap-friction-fit the barrel 78 of a conventional syringe of desired size, e.g., 3 cc (as FIGS. 9 and 10 also show).

The barrier material introducer/mixer 22 also includes a syringe clip 68. The syringe clip 68 includes spaced apart walls 70 forming an interior race 72. As FIGS. 9 and 10 show, the race 72 receives in a sliding friction fit the thumb rests 74 of the dispensing syringe pistons 76, in axial alignment with the syringe barrels 78 carried by the syringe support 64. The syringe clip 68 mechanically links the syringe pistons 76 together for common advancement inside their respective syringe barrels 78.

To faciliate handling (see FIGS. 2, 9 and 10), the syringe support 64 includes opposed finger rests 80, and the syringe clip 68 includes a thumb rest 82. The orientation of these rests 80 and 82 parallel the orientation of the finger rests and thumb rests of a single syringe. The physician is thereby able to hold and operate multiple syringes 60 and 62 in the same way as a single syringe.

The barrier material introducer/mixer 22 also includes a joiner 84. The joiner 84 includes side by side female luer fittings 86. The female luer fittings 86 each receives the threaded male luer fitting 88 at the dispensing end of the dispensing syringes 60 and 62. The female luer fittings 86 are axially aligned with the barrels 78 of the dispensing syringes 60 and 62 carried in the syringe support 64.

The physician is thereby able to quickly and conveniently ready the dispensing syringes 60 and 62 for use by securing the dispensing syringes to the joiner 84, snap fitting the syringe barrels 78 into the syringe support 64, and slide fitting the syringe thumb rests 74 into the clip 68.

The joiner 84 includes interior channels 90 coupled to the female luer fittings 86. The channels 90 merge at a Y-junction into a single outlet port 92. The joiner 84 maintains two fluids dispensed by the syringes 60 and 62 separately until they leave the joiner 84. This design minimizes plugging of the joiner 84 due to a mixing reaction between the two fluids. The syringe clip 68 ensures even application of individual solutions through the joiner 84.

The barrier material introducer/mixer 22 further includes a mixing chamber 94, which, in use, is coupled to the single outlet port 92 (as FIG. 10 shows). Expressed in tandem from the dispensing syringes 60 and 62, which are mechanically linked together by the joiner 84, support 64, and clip 68, the two components of the barrier material come into contact in the liquid state in the mixing chamber 94. Channel-mixing of the two components occurs as they flow through the mixing chamber 94 under pressure from operation of the mechanically linked dispensing syringes 60 and 62.

In the illustrated embodiment (see FIGS. 2 and 10), the mixing chamber 94 is carried at the end of a tube 96 attached to the handle 30 of the catheter device 20. The tube 96 communicates with interior lumens 134 in the catheter tube 24 (shown in FIG. 3), which, in turn, are coupled to the dispensing nozzles 34. The mixing chamber 94 includes a luer fitting 98, which threadably connects with the single outlet port 92 of the joiner 84.

The parts of the barrier material introducer/mixer 94 are made, e.g., by molding medical grade plastic materials, such as polycarbonate and acrylic.

II. Barrier Component Assembly The barrier component assembly 18 includes the already described dispensing syringes 60 and 62 for the two components of the barrier material.

According to the invention, the barrier material comprises a compound that is chemically cross-linked without the use of an enzyme, to form a non-liquid mechanical matrix.

As defined in this Specification, an "enzymatically cross-linked" barrier material is formed by the mixture of an enzyme and a substrate. Solutions of the substrate and enzyme can be delivered to the application site simultaneously, or separate solutions of the enzyme and substrate can be mixed at the application site. The enzyme cross-links to the substrate, transforming the solution to a solid. Examples of these materials include fibrin glue (in which the enzyme is thrombin and the substrate is fibrinogen), and transglutaminase cross-linked materials (in which the enzyme is transglutaminase and the substrate is selected from materials containing amino groups.

As further defined in this Specification, a "chemically cross-linked" barrier material refers to all barrier materials not formed through the use of enzymes. Cross-linking can occur, e.g., as a result of energy (heat or light), or cross-linking chemical reactions (active esters, isocyanates, epoxides). Examples of these materials includes photo-cross-linked acrylates and nucleophilic attack of electrophiles.

In a preferred embodiment, the barrier material is a protein/polymer composite hydrogel. The material is nontoxic, biodegradable, and possesses suitable mechanical properties to seal arterial pressure.

The barrier material is most preferably formed from the mixture of a protein solution and a solution of an electrophilic derivative of a hydrophilic polymer with a functionality of at least three. The barrier material of this composition has sufficient cohesive strength, adhesive strength, and elasticity to seal arterial pressure. The rate of cross-linking and gelation can be controlled through buffer selection and concentration. The rate of degradation after cross-linking can be controlled through the selection of a degradation control region.

A. Barrier Material Components

(i) Natural Plasma-Based Protein

In the illustrated embodiment (see FIG. 1), the first dispensing syringe 60 contains a concentration of buffered protein solution 100. The protein solution is supplemented with the appropriate buffers, sterile filtered, aseptically filled into the syringe 60, and the syringe 60 is capped for storage prior to use.

Suitable proteins for incorporation into barrier material include non-immunogenic, hydrophilic proteins. Examples include solutions of albumin, gelatin, antibodies, serum proteins, serum fractions, and serum. Also, water soluble derivatives of hydrophobic proteins can also be used. Examples include collagen, fibrinogen, elastin, chitosan, and hyaluronic acid. The protein can be produced from naturally occurring source or it may be recombinantly produced.

The preferred protein solution is 25% human serum albumin, USP. Human serum albumin is preferred due to its biocompatibility and its ready availability.

Buffer selection and concentration maintains the pH of the reactive mixture. Buffers that are well tolerated physiologically can be used. Examples include carbonate and phosphate buffer systems. Care should be taken to select buffers that do not participate in or interfere with the cross-linking reaction. The preferred range of buffer concentration is from about 0.01 M to about 0.3 M, and the preferred range of pH is from about 7.0 to about 10.0. A preferred buffer system for vascular puncture sealing is phosphate buffer at a concentration of 0.05 M at a pH value of about 8 to about 9. As will be described later, there is a relationship between pH and the time for cross-linking (also called "gelation").

As will be described in greater detail later, the syringe 60 is kept before use within inner and outer wraps, which are peripherally sealed by heat or the like. The wraps are made, at least in part, from a material that is permeable to ethylene oxide sterilization gas, e.g., TYVEK™ plastic material available from Du Pont. The outer surfaces of syringe 60 can thereby be sterilized using ethylene oxide gas.

(ii) Electrophilic Water Soluble Polymer

In the illustrated embodiment (still referring principally to FIG. 1), the second dispensing syringe 62 contains an inert, electrophilic, water soluble polymer 102. The polymer cross-links the protein to form an inert, three dimensional mechanical network or matrix. The matrix forms a mechanical barrier, which, when appropriately positioned in tissue at a vascular puncture site outside the vessel, serves to seal the puncture site. The barrier is, over time, resorbed.

The polymer 102 comprises a hydrophilic, biocompatible polymer, which is electrophilically derivatized with a functionality of at least three. A number of polymers could be utilized, including poly(ethylene glycol), poly(ethylene oxide), poly(vinyl alcohol), poly(vinylpyrrolidone), poly (ethyloxazoline), and poly(ethylene glycol)-co-poly (propylene glycol) block copolymers. The polymer portion is not restricted to synthetic polymers as polysaccharides, carbohydrates, and proteins could also be electrophilically derivatized.

Preferably, the polymer 102 is comprised of poly(ethylene glycol) (PEG) with a molecular weight between 1,000 and 30,000 g/mole, more preferably between 2,000 and 15,000 g/mole, and most preferably between 10,000 and 15,000 g/mole. PEG has been demonstrated to be biocompatible and non-toxic in a variety of physiological applications.

The preferred polymer can be generally expressed as compounds of the formula:

$$PEG-(DCR-CG)_n$$

where:
DCR is a degradation control region.
CG in a cross-linking group.
$n \geq 3$ While the preferred polymer is a multi-armed structure, a linear polymer with a functionality of at least three can also be used. The desired functionality of the PEG polymer for forming the barrier can be expressed in terms of (i) how quickly the polymer cross-links the protein and transforms to a nonfluent gel state (i.e., the mechanical barrier material) (a preferred gelation time is under three minutes), and (ii) the mechanical properties of the barrier after gelation in terms of its liquid sealing characteristics, physical strength, resistance to fragmentation (i.e., brittleness), and bioresorption. The optimization of both attributes (i) and (ii) is desirable.

The inventors have discovered that the utility of a given PEG polymer significantly increases when the functionality is increased to be greater than or equal to three. The observed incremental increase in functionality occurs when the functionality is increased from two to three, and again when the functionality is increased from three to four. Further incremental increases are minimal when the functionality exceeds about four.

The use of PEG polymers with functionality of greater than three provides a surprising advantage. When crosslinked with higher functionality PEG polymers, the concentration of albumin can be reduced to 25% and below. Past uses of difunctional PEG polymers require concentrations of albumin well above 25%, e.g. 35% to 45%. Use of lower concentrations of albumin results in superior sealing properties with reduced brittleness, facilitating reentry through the nonfluid barrier material, without fragmentation. Additionally, 25% human serum albumin, USP is commercially available from several sources, however higher concentrations of USP albumin are not commercially available. By using commercially available materials, the dialysis and ultrafiltration of the albumin solution, as disclosed in the prior art, is eliminated, significantly reducing the cost and complexity of the preparation of the albumin solution.

In the illustrated embodiment, the polymer 102 is initially packaged prior to use in the second dispensing syringe 92 in an inert atmosphere (e.g., argon) in a stable, powder form. In this arrangement, the barrier component assembly 18 includes a third syringe 104, which contains sterile water 106 for dissolution of the powder polymer 102 just before mixing with the albumin component 100.

In facilitating mixing, a stopcock valve 108 is secured to the luer fitting 88 at the dispensing end of the second dispensing syringe 62. The dispensing end 110 of the water syringe 104 couples to the stopcock valve 108, so that the water 106 can be mixed with the polymer 102 in the dispensing syringe 72 prior to use. Further details of the preparation of the polymer prior to use will be described later.

In the illustrated embodiment, the second and third dispensing syringes 62 and 104 are placed in inner and outer wraps peripherally sealed by heat. The wraps are made, at least in part, from a material that is transparent to electron beam irradiation. The contents of the second and third dispensing syringes 62 and 104 can thereby be sterilized, e.g., by exposure to electron beam irradiation.

(a) Selection of the Degradation Control Region DCR

The rate of degradation is controlled by the selection of chemical moiety in the degradation control region DCG. If degradation is desired, a hydrolytically or enzymatically degradable moiety can be selected, Examples of hydrolytically degradable moieties include saturated di-acids, unsaturated di-acids, poly(glycolic acid), poly(DL-lactic acid), poly(L-lactic acid), poly(ξ-caprolactone), poly(δ-valerolactone), poly(γ-butyrolactone), poly(amino acids), poly(anhydrides), poly(orthoesters), poly (orthocarbonates), and poly(phosphoesters).

Examples of enzymatically degradable regions include Leu-Glyc-Pro-Ala (collagenase sensitive linkage) and Gly-Pro-Lys (plasmin sensitive linkage).

The preferred degradable control regions for degradable barrier materials are ester containing linkages, as are present-when succinic acid or glutaric acid are coupled to a PEG molecule. The preferred degradable control regions for nondegradable barrier materials are ether containing linkages. The barrier material can also be created without the introduction of a degradation control region.

(b) Selection of the Cross-Linking Group CG

The cross-linking group is responsible for the cross-linking of the albumin, as well as the binding to the tissue substrate. The cross-linking group can be selected to selectively react with sulfhydryl groups, selectively react with amines, or can be selected to react with sulfhydryl, primary amino, and secondary amino groups. Cross-linking groups that react selectively with sulfhydryl groups include vinyl sulfone, N-ethyl maleimide, iodoacetamide, and orthopyridyl disulfide. Cross-linking groups specific to amines include aldehydes. Non-selective electrophilic cross-linking groups include active esters, epoxides, carbonylimidazole, nitrophenyl carbonates, tresylate, mesylate, tosylate, and isocyanate. The preferred cross-linking group is an active ester, specifically an ester of N-hydroxysuccinimide.

To minimize the liberation of heat during the cross-linking reaction, the concentration of the cross-linking groups is preferably kept less than 5% of the total mass of the reactive solution, and more preferably about 1% or less. The low concentration of the cross-linking group is also beneficial so that the amount of the leaving group is also minimized. In a preferred embodiment, the cross-linking group portion comprising a N-hydroxysuccinimide ester has demonstrated ability to participate in the cross-linking reaction with albumin without presenting the risk of local or systemic immune responses in humans.

(c) Preferred Multiple Arm PEG Polymer

In a preferred embodiment, the polymer is comprised of a 4-arm PEG with a molecular weight of about 10,000 g/mole, the degradation control region is comprised of glutaric acid, and the cross-linking group is comprised of a N-hydroxysuccinimide ester. Thus, a preferred polymer is poly(ethylene glycol) tetra-succinimidyl glutarate, which is available from Shearwater Polymers, Huntsville, AL. The preferred polymer-will, in shorthand, be called 4-PEG-SG. The polymer is dissolved in water prior to use. Preferred concentrations of the polymer are from 5% to 35% w/w in water.

The solution of 4-PEG-SG mixes with 25% serum albumin to form a liquid solution that quickly cross-links to form a non-liquid, three dimensional network for the barrier. With these barrier material formulations, it is possible to intimately mix the water soluble polymer with the albumin protein without static mixing. Effective mixing occurs as the multiple arm PEG polymer and albumin are jointly passed through a confined flow path. This beneficial phenomenon has been earlier referred to in this specification as "channel-mixing."

As will be demonstrated later, the rate of reaction can be controlled by the pH of the reactive solution. An increase in temperature is not observed during formation of the barrier network, due to the low concentration of reactive groups, which account for only about 1% of the total mass. In a typical clinical application, about 50 mg of a non-toxic leaving group is produced during the cross-linking reaction, which is a further desired result.

The resulting nonfluent barrier material created by mixing 25% albumin and 4-PEG-SG is approximately 80% water, 13% albumin, and 7% PEG. The barrier material is well tolerated by the body, without invoking a severe foreign body response. Over a controlled period of time, the barrier material is degraded via hydrolysis. Histological studies have shown a foreign body response consistent with a biodegradable material, such as VICRYL™ sutures. As the material is degraded. The tissue returns to a quiescent state. The molecules of the degraded barrier material are cleared from the bloodstream by the kidneys and eliminated from the body in the urine. In a preferred embodiment of the invention, the barrier material loses its physical strength during the first twenty days, and total resorption occurs in about 4 weeks.

The following Examples demonstrate the superior features of the barrier material of the invention.

EXAMPLE 1

Preparation of Cross-Linked Barrier Networks

Cross-linked barrier networks were formed by the mixture of an 4-PEG-SG and albumin. A solution of 4-PEG-SG was prepared by dissolving 0.40 g in 2.0 mL of water. The albumin solution consisted 25% human serum alburmin, USP (Plasbumin-25, Bayer Corporation), as received.

Dispensing syringes containing 2.0 mL of the polymer solution and 2.0 mL of albumin solution were connected to the joiner 84, to which a spray head was coupled. The solutions were sprayed into a polystyrene weigh boat. A cross-linked barrier network formed at room temperature in about 90 seconds.

EXAMPLE 2

Control of the Rate of Gelation

The rate of formation of the cross-linked barrier network of 4-PEG-SG and albumin (i.e., gelation) can be controlled by the pH of the reactive solution. To increase the rate of cross-linking, the pH of the solution is increased, and conversely, to decrease the rate of cross-linking, the pH of the solution is decreased. The pH of the solution is controlled by both the buffer strength and buffer pH.

Table 1 shows the effect of buffer strength on the rate of gelation of 17% w/w 4-PEG-SG in water for injection and 25% human serum albumin, USP at room temperature. The rate of gelation can also be controlled by adjusting the pH of the buffer at a constant buffer concentration. The buffer was placed in the solution of albumin. The gelation time is the amount of time required for the formulation to transform from the liquid state to the cross-linked solid state.

TABLE 1

Effect of Buffer Strength and Buffer pH an Gel Formation

| Buffer Concentration | Buffer pH | Gelation Time |
|---|---|---|
| 300 mM | 9 | <1 sec |
| 200 mM | 9 | 5 sec |

TABLE 1-continued

Effect of Buffer Strength and Buffer
pH an Gel Formation

| Buffer Concentration | Buffer pH | Gelation Time |
| --- | --- | --- |
| 100 mM | 9 | 10 sec |
| 50 mM | 9 | 20 sec |
| 0 mM | 7 | 90 sec |

EXAMPLE 3

Channel-Mixing

A solution of 4-PEG-SG was prepared by dissolving 0.40 g in 2.0 mL of water. The albumin solution consists 25% human serum albumin, USP (Plasbumin-25, Bayer Corporation), buffered to pH 9.0.

Syringes containing 2.0 mL of the polymer solution and albumin solution were connected to the joiner 84. A cannula channel having an inside diameter of 1 mm and a length of 20 cm was attached to the outlet port 92 of the joiner 84. The solutions were expressed through the cannula channel into a polystyrene weigh boat.

The barrier network formed at room temperature in about 20 seconds. Qualitatively, the mechanical properties of the barrier network when sprayed (as in Example 1) and the barrier network when expressed through the cannula channel were equivalent.

This demonstrates that the barrier network can be formed by channel-mixing the liquid components, without static mixing, by delivery through a small diameter channel.

III. Puncture Site Closure Using the System

A. The Kits

Figure 7A:
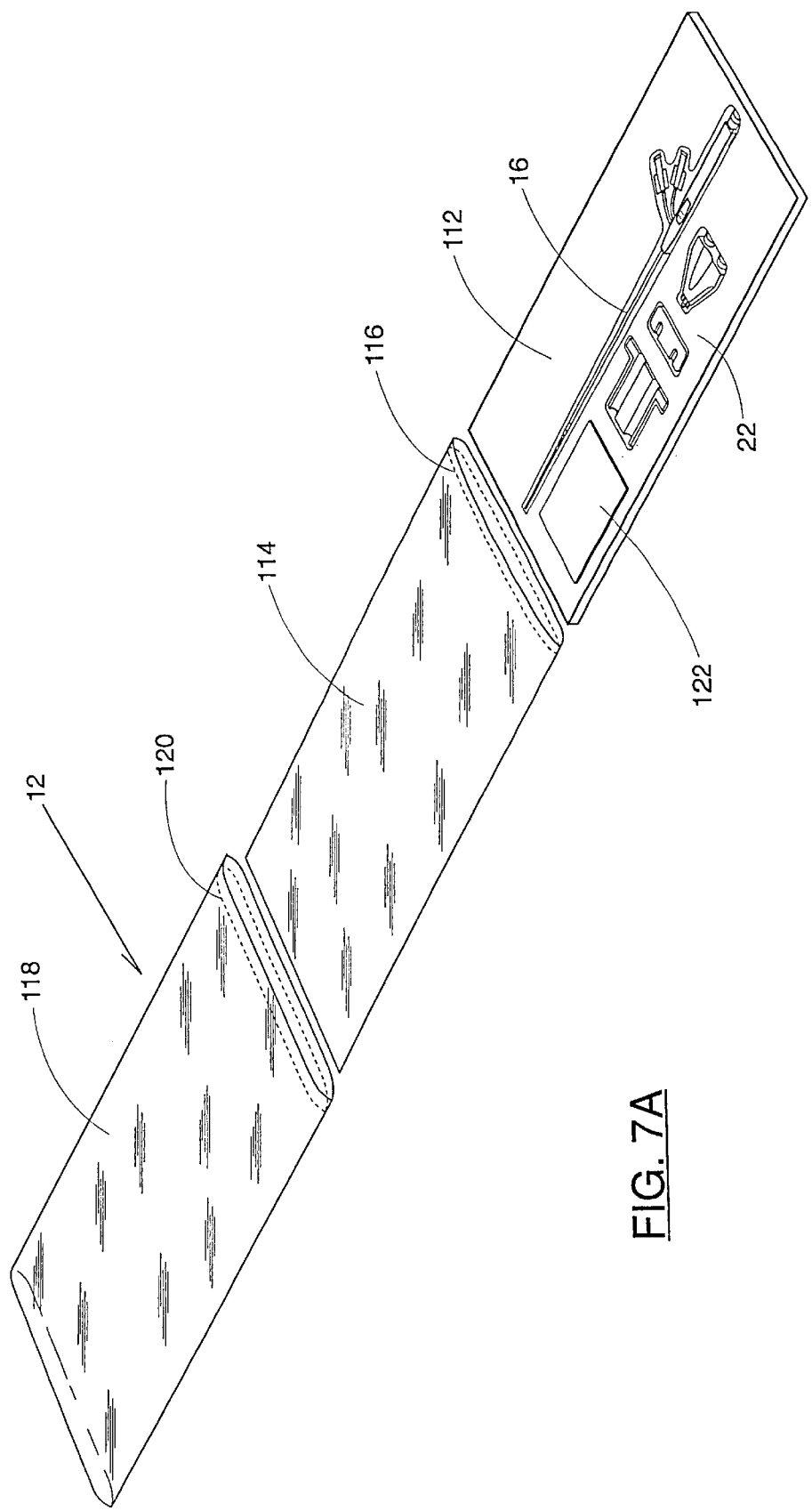
FIG. 7A is an exploded, perspective view of the site access kit shown in FIG. 1.
Figure 7B:
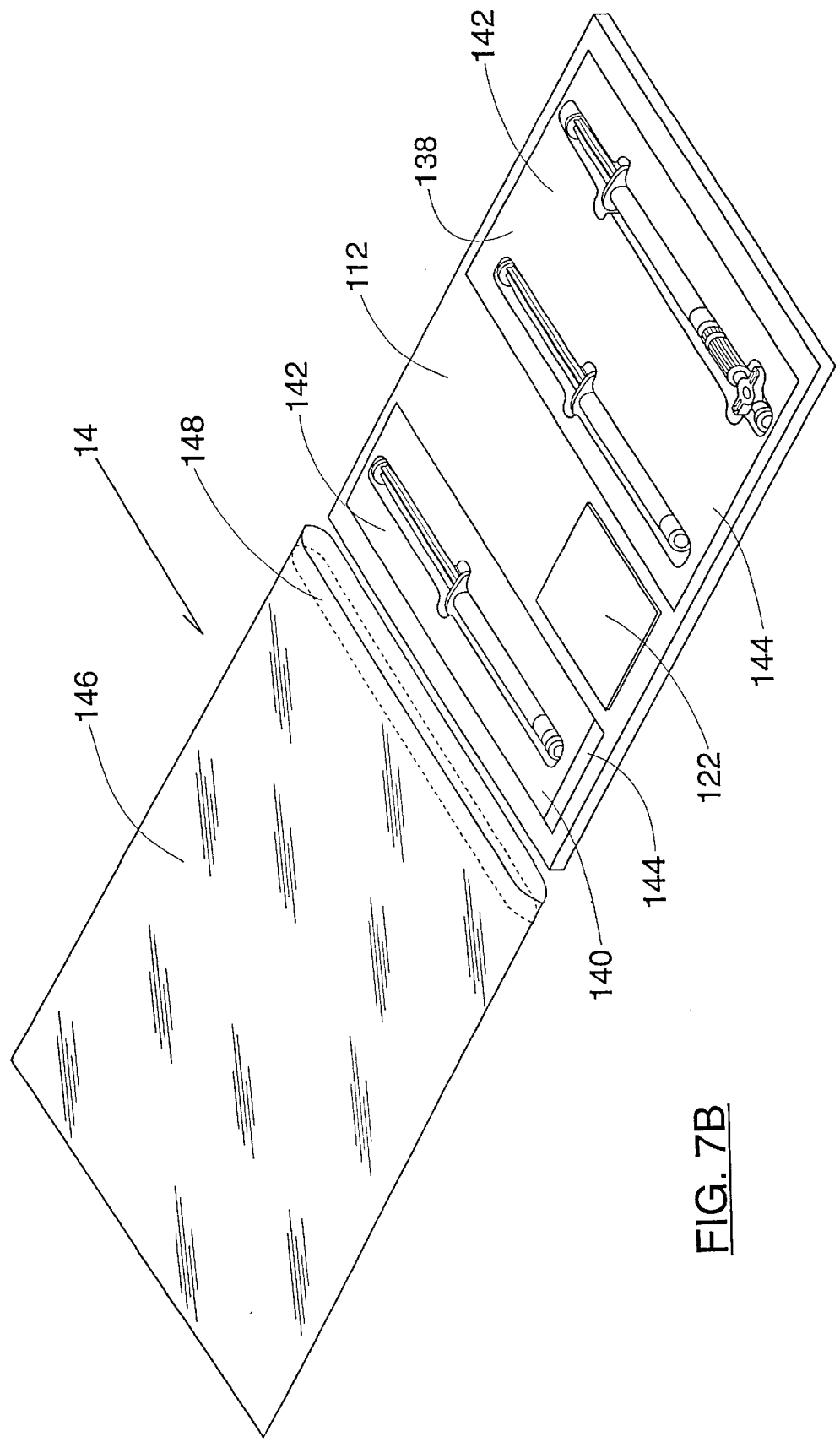
FIG. 7B is an exploded, perspective view of the barrier component kit shown in FIG. 1.

As FIGS. 7A and 7B show, in the illustrated embodiment, each kit 12 and 14 includes an interior tray 112 made, e.g., from die cut cardboard, plastic A sheet, or thermo-formed plastic material.

The catheter device 20 and barrier material introducer/mixer 22 are carried by the tray 112 in the first kit 12. The first, second, and third syringes 60, 62, and 114 and stopcock valve 108 are carried by the tray 112 in the second kit 14.

Each kit 12 and 14 presents its contents in a user-friendly orientation on the tray 112, to facilitate quick preparation of the barrier material using straightforward, intuitive steps, and the subsequent attachment of the dispensing syringes 60 and 62 to the catheter device 20.

As shown in FIG. 7A, the kit 12 includes an inner wrap 114, which is peripherally sealed by heat or the like, to enclose the tray 112 from contact with the outside environment. One end of the inner wrap 114 includes a conventional peel away seal 116. The seal 116 provides quick access to the tray 112 at the instant of use, which preferably occurs in a suitable environment, such as within a catheterization lab.

The kit 12 is further wrapped in an outer wrap 118, which is also peripherally sealed by heat or the like, to enclose the interior tray 112. One end of the inner wrap 118 includes a conventional peel away seal 120, to provide quick access to the interior tray 112 and its contents.

The outer wrap 118 and the inner wrap 114 are made, at least in part, from a material that is permeable to ethylene oxide sterilization gas, e.g., TYVEK™ plastic material (available from DuPont). Kit 12 is sterilized utilizing ethylene oxide gas or electron beam irradiation.

As shown in FIG. 7B, kit 14 includes a polymer package 138 (which contains the prefilled powder polymer syringe 62 and water syringe 104) and an albumin package 140 (which contains the prefilled albumin syringe 64). Each polymer package 138 and albumin package 140 includes an individual wrap 142, which is peripherally sealed by heat or the like, to enclose package 138 and 140 from contact with the outside environment. One end of the individual wrap 142 includes a conventional peel away seal 144, to provide quick access to the contents of the packages 138 and 140 at the instant of use, such as within a catheterization lab.

Polymer package 138 and albumin package 140 are further wrapped in an outer wrap 118, which is also peripherally sealed by heat or the like. One end of the outer wrap 118 includes a conventional peel away seal 148, to provide quick access to the packages 138 and 140. After sterilization treatment, the packages 138 and 140 and the tray 112 are further wrapped in container 146 for the user's convenience.

The wraps 142 and 118 are made, at least in part, from a material that is permeable to ethylene oxide sterilization gas, e.g., TYVEK™ plastic material (available from DuPont). The albumin package 140 is prepared, sterilized utilizing ethylene oxide gas, and placed into kit 14. The polymer package 138 is prepared, sterilized utilizing electron beam irradiation, and place into kit 14.

In the illustrated embodiment, each kit 12 and 14 also preferably includes directions 122 for using the contents of the kit to carry out a desired procedure. Exemplary directions 122 will be described later.

B. Use of the Kits to Access and Seal a Vascular Puncture Site

The directions 122 can, of course vary, according to the particularities of the desired procedure. Furthermore, the directions 122 need not be physically present in the kits 12 and 14. The directions 122 can be embodied in separate instruction manuals, or in video or audio tapes.

In the illustrated embodiment, exemplary directions 122 are described, which instruct the physician how to use of the system 10 to close a vascular puncture site following percutaneous transluminal coronary angioplasty. It should be appreciated that the specific contents of the directions 122 are merely exemplary. The objectives set forth in the exemplary directions 122 can be accomplished in different ways, using different devices, and different sequences of steps.

It should also be appreciated that the use of the system 10 is not limited to angioplasty procedures. The system 10 can be used with other diverse procedures, which provide vascular access through a puncture site.

In the illustrated embodiment, at the time the system 10 is readied for use, the guide wire 40 has already been deployed through a conventional introducer through a vascular puncture site into, e.g., the femoral artery. An angioplasty balloon has been deployed over the guide wire 40 through the puncture site and into the artery. The angioplasty balloon has been advanced over the guide wire 40 to the occluded treatment site. The balloon has been expanded and manipulated to open the occluded site. The balloon has been withdrawn over the guide wire 40.

When use of the system 10 is desired, the outer wrap 118 of the kits 12 and 14 are removed. The trays 112, still contained in the inner wraps 118, are placed in the sterile operating field.

The physician opens the inner wrap 118 of the second kit 14 to gain access the first, second, and third syringes 60, 62, and 104.

In the illustrated embodiment, the directions 122 for use instruct the physician to remove from the second kit tray 112 the second dispensing syringe 62, which contains, in sterile powder form, a predetermined amount of the polymer 102 (e.g., about 0.3 to 0.5 g). The directions 122 also instruct the physician to remove from the second kit 14 the third syringe 104, which contains sterile water 106 (e.g., about 2 cc). Both are contained in the polymer package 138.

As FIG. 8A shows, the directions 122 instruct the physician to couple the dispensing end of the water syringe 104 to the stopcock valve 108 on the second dispensing syringe 62. The stopcock valve 108 is closed at this point. As instructed by the directions 122, the physician opens the stopcock valve 108 (see FIG. 5B) and transfers water from the water syringe 104 into the powder 100 in the second dispensing syringe 62 (see FIG. 8C). The physician is instructed to repeatedly transfer the water and powder mixture between the two syringes 62 and 104, to syringe-mix the powder and water until all solids are dissolved. The syringe-mixing places the water soluble, polymer material into solution. The syringe-mixing process generally takes about two minutes.

After syringe mixing, the physician, following the directions 122, transfers the PEG solution 136 (about 2 cc) into one of the syringes (which, in the illustrated embodiment, is the second syringe 62). The physician waits for bubbles to dissipate, which generally takes about an additional two minutes.

According to the directions 122, the physician now closes the stopcock valve 108 (as FIG. 8D shows). The physician removes the stopcock valve 108 by unscrewing it from the luer fitting on the dispensing end of the second syringe 62. The PEG solution 136 is ready for use. Mixing of the PEG solution 136 should take place generally within one hour of use. If the PEG solution 136 remains unused over one hour after mixing, it should be discarded.

The directions 122 instruct the physician to remove from the second kit tray 112 the dispensing syringe 60 containing the albumin 100. As before described, the albumin 100 has been premixed in a buffered form to the desired concentration (e.g., 25%), then sterile filtered, and aseptically filled into the syringe 60. A closure cap normally closes the dispensing end inside the tray 112.

The physician now, or at a previous time, opens the outer wrap 118 of the first kit 12 to gain access to the catheter device 20 and barrier material introducer/mixer 22. Using an auxiliary syringe (not shown), the physician is instructed to instructed to flush the interior lumen leading to the nozzles 34 with sterile saline. The physician is also directed to flush the interior guidewire lumen 32 with sterile saline. The physician attaches another auxiliary syringe 126 filled with about 1 cc of air to the fitting 54 for inflating the deformable region 44 to confirm its functionality, and then returns the deformable region 44 to the collapsed state.

As illustrated in FIG. 9, the directions 122 instruct the physician to remove the closure cap and screw the dispensing end of the first syringe 60 to the luer fitting 86 on the joiner 84. The physician is also instructed to screw the dispensing end of the second syringe 62 (now containing the mixed PEG Asolution 136) to the other luer fitting 86 on the joiner 84.

Following the directions 122 (as FIG. 9 also shows), the physician snaps the barrels 78 of the syringes 60 and 62 to the holder channels 66. The physician captures the thumb rests 74 of the two syringes 60 and 62 inside the race 72 of the syringe clip 68. The directions 122 instruct the physician to attach the joiner 84 to the mixing channel 94 (as FIG. 10 shows).

The physician is now ready to deploy the catheter tube 24. As FIG. 5 shows, the physician is instructed to pass the distal end 28 of the catheter tube 24 over the guide wire 40 through the puncture site. The physician advances the distal end 28 to situate the first deformable region 38 inside the vessel, while the nozzles 34 are deployed outside the vessel. The physician can monitor the advancement tactilely, without using fluoroscopy. However, the physician can use fluoroscopy or an other form of visualization, if desired.

According to the directions 122 (as FIG. 6 shows), the physician pulls the lever 50 rearward, causing the first deformable region 38 to expand radially into the positioner 42. The physician is instructed to place slight rearward tension on the catheter tube 24 (shown by arrow 132 in FIG. 6), to bring the positioner 42 into contact with the interior of the vessel. The physician will, by tactile feedback, know that the positioner 42 has contacted the vessel interior. Due to the slight rearward tension, the positioner 42 seats against and supports the puncture site. The guide wire lumen 32 of the catheter tube 24 can be used to inject suitable contrast media to aid in the visualization of the puncture site region.

While maintaining slight rearward tension on the catheter tube 24, the physician is instructed to manipulate the syringe 126 to inject air (e.g. about 0.7 cc to 0.8 cc) into the second deformable region 44. The second deformable region 44 expands (as FIG. 6 shows), forming the dam 46 outside the vessel.

The physician is instructed to continue to apply a slight rearward tension on the catheter tube 24, sufficient to keep the positioner 42 against the interior of the vessel, without pulling it through the vessel wall.

The physician is instructed to grasp the finger rests 80 and thumb rest 82 of the barrier material introducer/mixer 22, as if grasping an ordinary syringe. The physician expresses the albumin 100 from the first dispensing syringe 60 while simultaneously also expressing the PEG solution 136 from the second dispensing syringe 62.

The albumin and PEG solutions come into contact in the mixing chamber 94 and, from there, proceed through the catheter tube 24 to the nozzles 34. The albumin 100 and PEG solution 136 intimately channel-mix in transit.

Figure 11:
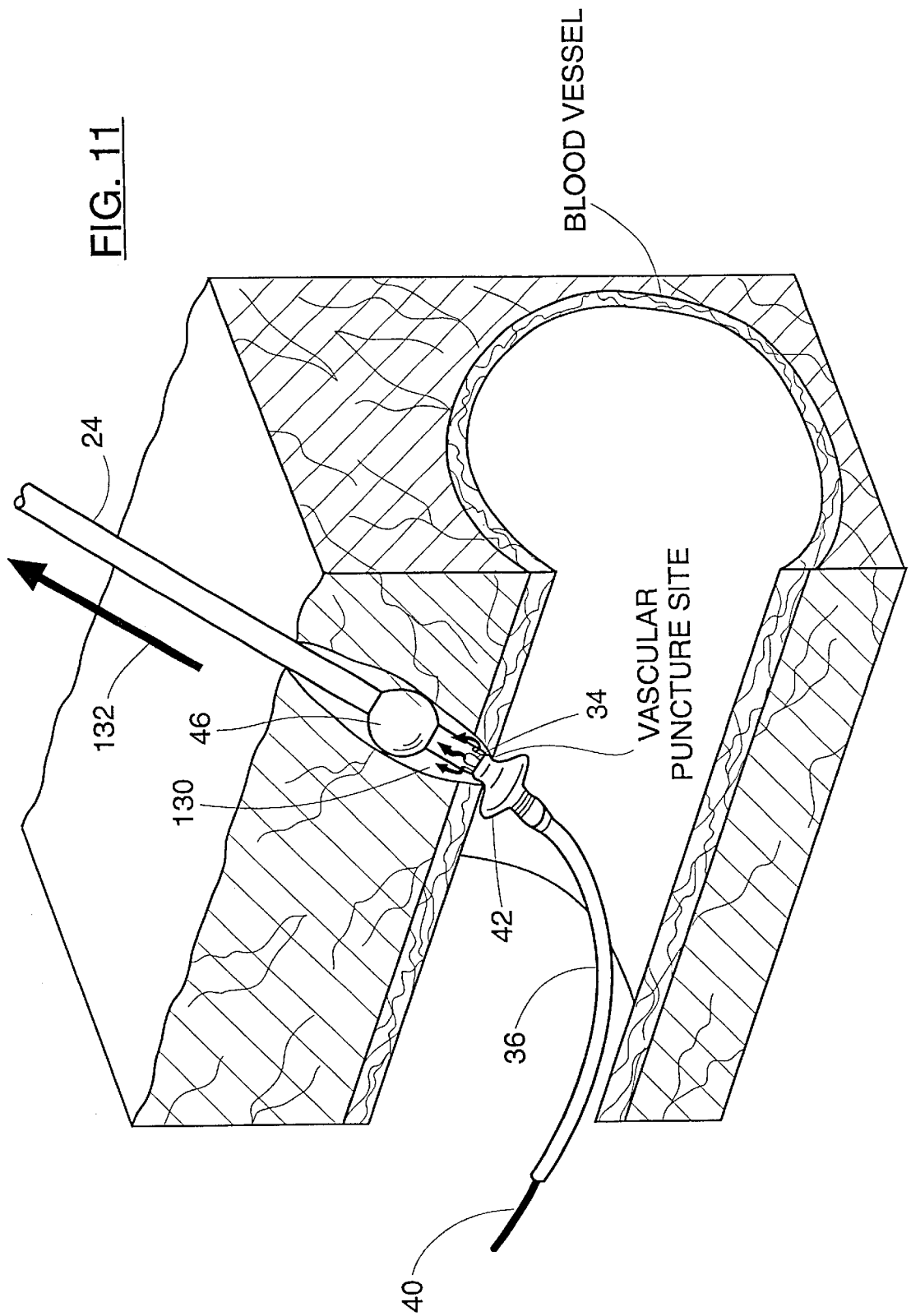
FIG. 11 is a schematic, perspective view of the vascular puncture site shown in FIG. 6, as the barrier material introducer/mixer is being operated to convey a liquid mixture of albumin and PEG solution into a tissue region outside the puncture site.

As FIG. 11 shows, the mixture of albumin 100 and PEG solution 136 flows in liquid form through the nozzles 34. conveyed circumferentially about the catheter tube 24 by the nozzles 34, the liquid mixture 130 of albumin 100 and PEG solution 136 enters and fills the tissue region surrounding the puncture site.

Figure 12:
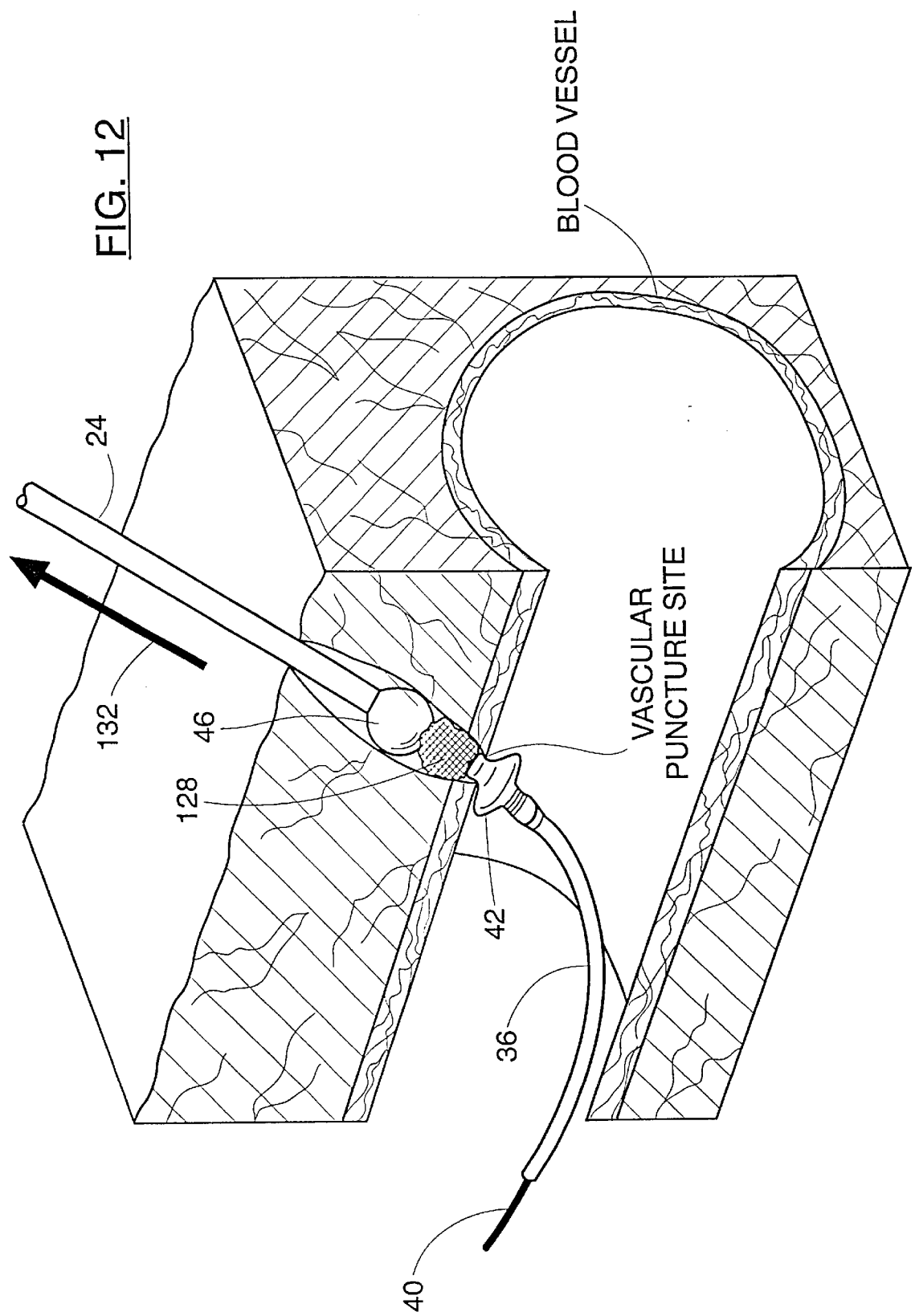
FIG. 12 is a schematic, perspective view of the vascular puncture site shown in FIG. 11, as the the liquid mixture of albumin and PEG solution cross-links to form a non-liquid barrier network in the tissue region outside the puncture site.

As FIG. 12 shows, according to the directions 122, the physician waits the requisite gelation period, during which the liquid mixture 130 of albumin 100 and PEG material 136 transform into a non-fluid barrier network 128 outside the puncture site. Using 4-PEG-SG and albumin, the gelation period is about 15 to 60 seconds. .

During the gelation period, the physician is instructed to continue to apply a slight rearward tension on the catheter tube 24 to seat the positioner 42 against the interior vessel wall. This, in effect, suspends the vessel on the distal end of the catheter tube 24, while the solid barrier network 128 forms outside the vessel to seal the puncture site. The positioner 42 and the catheter tube 24 resist seepage of the liquid mixture 130 into the vessel during the gelation period.

After the requisite gelation period, the physician is instructed to push the lever 50 forward to relax the positioner 42. The physician also relieves air pressure from the dam 46. The physician withdraws the guide wire 40 and the distal end 28 of the catheter tube 24 from the vessel. As shown by FIG. 13, during withdrawal, the distal end 28 and the guide wire 40 pass through the barrier network 128 that has, by now, formed over the puncture site. If desired, the guidewire 40 may be left in place for removal at a future time.

After withdrawing the catheter tube 24, the physician is instructed to apply manual pressure to the skin over the blood vessel, e.g., for about three minutes, to aid in the sealing process. This time allows the barrier material to fully cross-link. The physician then confirms that the puncture site has been sealed by observing the lack of blood seepage about the guide wire 40 access.

The puncture site of the vessel naturally closes and heals. As FIG. 13 shows, the presence of the barrier network 128 outside the puncture site m prevents blood leakage while natural healing takes place. The barrier network 128 obviates the need for the patient to forgo ambulation and normal activities while this natural healing process takes place. The body resorbs the barrier network 128 over time, e.g., within 30 days.

EXAMPLE 4

Femoral Puncture Site Closure

A solution of 4-arm PEG succinimidyl glutarate, MW 10,000 (Shearwater Polymers, Huntsville, Ala.) was prepared by dissolving 0.40 g in 2.0 mL of water for injection. The albumin solution consists 25% human serum albumin, USP (Plasbumin-25, Bayer Corporation), buffered to pH 9.0.

Syringes containing 2.0 mL of the polymer solution and 2.0 mL of albumin solution were connected to the joiner coupled to the catheter device having an 8 French catheter tube 24.

Aseptically, the distal end of the catheter tube 24 was inserted into the femoral artery of a sedated sheep. The first and second deformable regions were enlarged inside and outside the artery. The material in the dispensing syringes were simultaneously injected through the mixing chamber into the catheter tube 24, and dispensed through the nozzles 34 at the tissue site.

Twenty seconds was allowed for gelation. The deformable regions were relaxed, and the catheter tube 24 was withdrawn from the artery.

Direct pressure was applied to the artery for an additional 3 minutes to allow the barrier material to fully harden. When the pressure was relieved, blood loss through the tissue track or hematoma formation was not observed. Doppler analysis confirmed blood flow distally from the arteriotomy. The time between application of liquid barrier material to the formation of a non-liquid barrier to affect complete sealing was 3.5 minutes.

The treated sheep was upright and bearing weight evenly on its legs within 45 minutes after deployment of the barrier material. After about one hour from the completion of the procedure, hay was placed in the pen. The sheep immediately began eating. Approximately 2 hours after the procedure, the animal was bright, alert, and responsive without a hematoma. The animal did not exhibit any adverse effects from the treatment and was indistinguishable from non-treated sheep.

Thirty days post-operative, the animal was sacrificed and the femoral artery was removed en bloc, placed in formalin, and evaluated using standard histological techniques. Approximately 10% of the implanted material was still remaining at thirty days. The evaluating pathologist noted a foreign body response to the material that was consistent with a biodegrading material. Additional studies have shown that, after the material has entirely degraded, the tissue returns to a quiescent state.

EXAMPLE 5

Additional Femoral Puncture Site Closure Procedures in Sheep

A number of additional procedures have been performed using the barrier material in various sizes of puncture sizes using heparinized sheep. The following Table summarizes the results:

TABLE 2

Femoral Sealing Results (Heparinized Sheep)

| Barrier Material | Catheter tube 24 Diameter | Number of Procedures | Bleeding Stopped in less than 3 minutes (Measured Between Material Application and When Bleeding Stopped) | Total Procedure Time Less than 10 Minutes (Measured Between Insertion of Catheter Tube and Stoppage of Bleeding After Removal of Catheter Tube) |
|---|---|---|---|---|
| 4-arm PEG/Albumin | 6 Fr | 1 | 1 of 1 | Not Applicable |
| 4-arm PEG/Albumin | 8 Fr | 3 | 2 of 3 | 3 of 3 |
| 4-arm PEG/Albumin + Heparin | 8 Fr | 3 | 2 of 3 | 3 of 3 |

EXAMPLE 6

Additional Femoral Puncture Site Closure Procedures in Pigs

A number of additional procedures have been performed using the barrier material in various sizes of puncture sizes in pigs. The procedure used in the porcine experiments is identical to that used in the ovine experiments.

The following Table summarizes the results.

TABLE 3

Femoral Sealing Results (Pigs)

| Barrier Material | Catheter tube 24 Diameter | Number of Procedures | Bleeding Stopped in less than 3.5 minutes (Measured Between Material Application and When Bleeding Stopped) | Total Procedure Time Less than 10 Minutes (Measured Between Insertion of Catheter Tube and Stoppage of Bleeding After Removal of Catheter Tube) |
|---|---|---|---|---|
| 4-arm PEG/Albumin | 8 Fr | 4 | 3 of 4 | 4 of 4 |
| 4-arm PEG/Albumin | 7 Fr | 1 | 1 of 1 | Not Applicable |

IV. Alternative Embodiments

A. Catheter Device

FIG. 14 shows an alternative embodiment of a catheter device 220 that the system 10 can incorporate instead of the catheter device 20.

Like the catheter device 20, the catheter device 220 includes a flexible catheter tube 224 having a proximal end 226 and a distal end 228. The catheter tube 224 can be constructed from the same medical grade plastic materials as the catheter tube 24, already described. As with the catheter tube 24, the distal end 228 has an outside diameter of, e.g., 4 Fr to 16 Fr. Unlike the distal end 28, the distal end 228 has a uniform diameter along its entire length, which also matches the outside diameter of the entire catheter tube 24.

The proximal end 226 carries a handle 230 to facilitate gripping and maneuvering the catheter tube 224 by a physician. As shown in FIG. 14, the handle 230 is of reduced size, compared to the handle 30. The reduced size of the handle 230 facilitates holding the handle 330 between the forefinger and thumb, for better fine control and tactile feedback.

As FIG. 16 shows, an interior lumen 232 extends through the catheter tube 224. The lumen accommodates passage of a conventional guide wire 40, as already described.

Like the catheter device 20, the catheter device 220 includes, at its distal end 228, a circumferentially spaced array of nozzles 234 (see FIG. 15). The barrier material is conveyed in liquid form and dispensed in a circumferential manner through the nozzles 234 at the puncture site.

As FIG. 15 shows, the distal end 228 includes a single deformable region 238, which is located a short distance from the nozzles 234. Unlike the catheter device 20, the distal end 228 of the catheter device 220 does not includes a leader, extending distally from the deformable region 238. The distal end 228 terminates a short distance from the deformable region 238.

Figure 17:
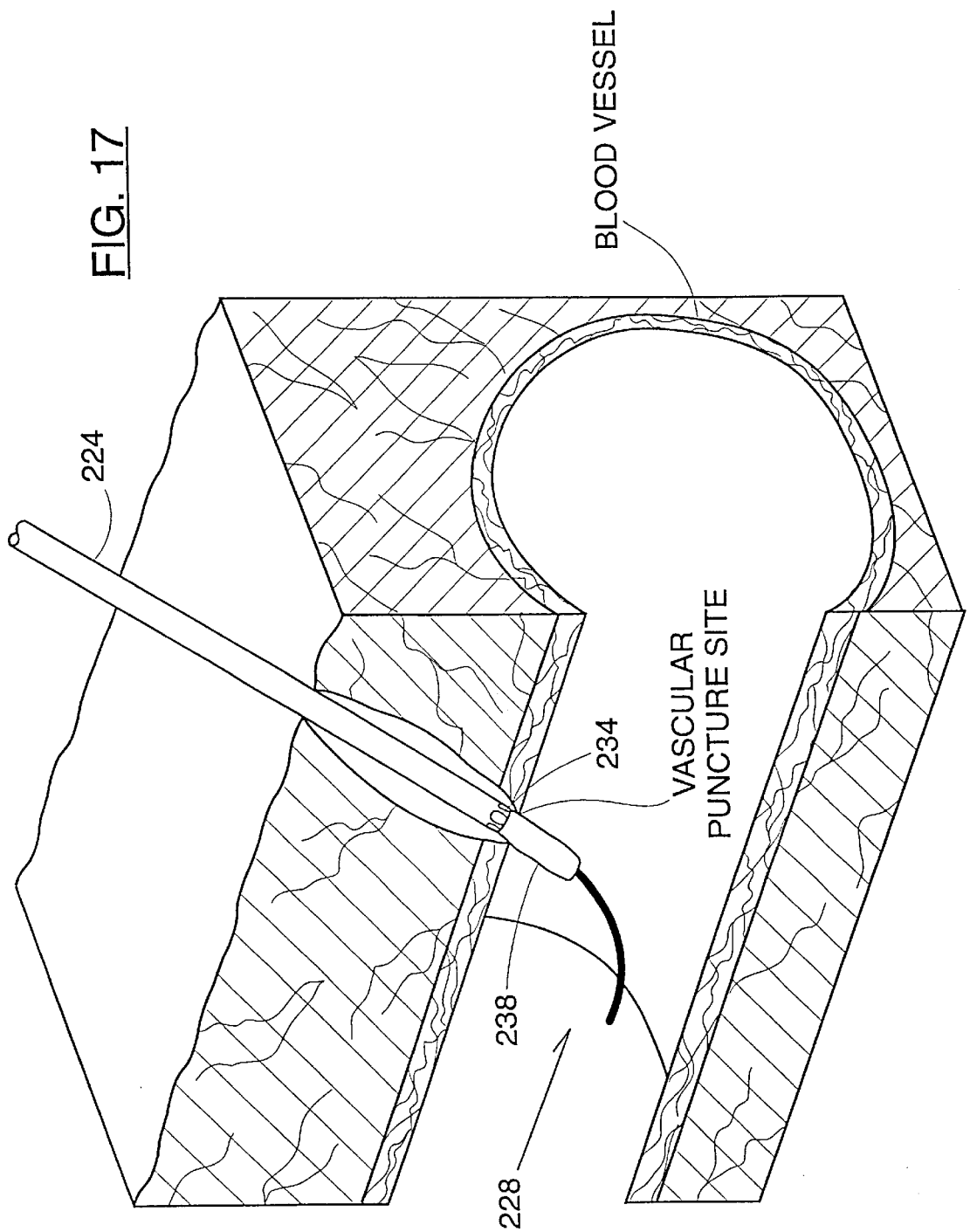
FIG. 17 is a schematic perspective view of the distal end of the catheter device shown in FIG. 14, when deployed in the collapsed condition at a vascular puncture site.

The deformable region 238 normally presents a generally cylindrical, low profile condition (shown in FIG. 14), presenting an outside diameter that is generally the same as the distal end 238 itself. When the low profile condition, the region 238 passes over the guide wire into the vessel (as FIG. 17 shows).

The region 238 can be deformed into a radially enlarged condition, which forms a positioner 242 (see FIG. 15). In use (see FIG. 18), the positioner 242 resists passage through the puncture site in response to rearward tension along the catheter tube 224, as shown by arrow 132 in FIG. 18. The positioner 242 serves to position the nozzles 234 at a proper distance outside the vessel, while the liquid barrier material is introduced outside the vessel through the nozzles 34.

Unlike the catheter device 20, the catheter device 220 does not include a second deformable region spaced proximal to the nozzles 34. It has been found that the gelation of the liquid barrier material, as described above, occurs quickly enough to obviate the need for a proximal dam.

The deformation of the region 238 can be accomplished in various ways. In the illustrated embodiment, the region 238 comprises an expandable balloon material attached about the catheter tube 224. The catheter tube 224 includes an interior lumen 256 (shown in FIG. 16), which communicates through an aperture 258 with the interior of the balloon material. A fitting 254 carried by the handle 230 (see FIG. 14) communicates with the lumen 256. The fitting 254 couples the lumen to an auxiliary syringe 126, which injects air under pressure through the lumen 256 into the space surrounded by the balloon material, causing the material to expand and form the positioner 242.

As FIG. 14 shows, a mixing chamber 294 is carried at the end of a tube 296 attached to the handle 230 of the catheter device 220. The tube 296 communicates with interior lumens 334 in the catheter tube 224 (shown in FIG. 16), which, in turn, are coupled to the dispensing nozzles 234. The mixing chamber 294 includes a luer fitting 298, which threadably connects with the single outlet port 92 of the joiner 84 (see FIG. 17).

In use, the barrier material introducer/mixer 22 expresses the albumin 100 and polymer solution 136 in tandem from the dispensing syringes 60 and 62, which are mechanically linked together by the joiner 84, support 64, and clip 68, in the manner already described. The two components of the barrier material come into contact in the liquid state in the mixing chamber 294. Channel-mixing of the two components occurs as they flow through the mixing chamber 294 to the nozzles 234.

Prior to deploying the catheter device 220 for use, the physician prepares the PEG solution 136, and couples the syringes 60 and 62 to the barrier introducer/mixer 22, in the manners previously described.

As FIG. 17 shows, according to appropriate instructions 122, the physician is instructed to pass the distal end 228 of the catheter tube 224 over the guide wire 40 through the puncture site. The physician advances the distal end 228 to situate the deformable region 238 inside the vessel, while the nozzles 234 are deployed outside the vessel. The physician can monitor the advancement tactilely. The presence of the uniform diameter distal end 228 seals the puncture site.

Figure 18:
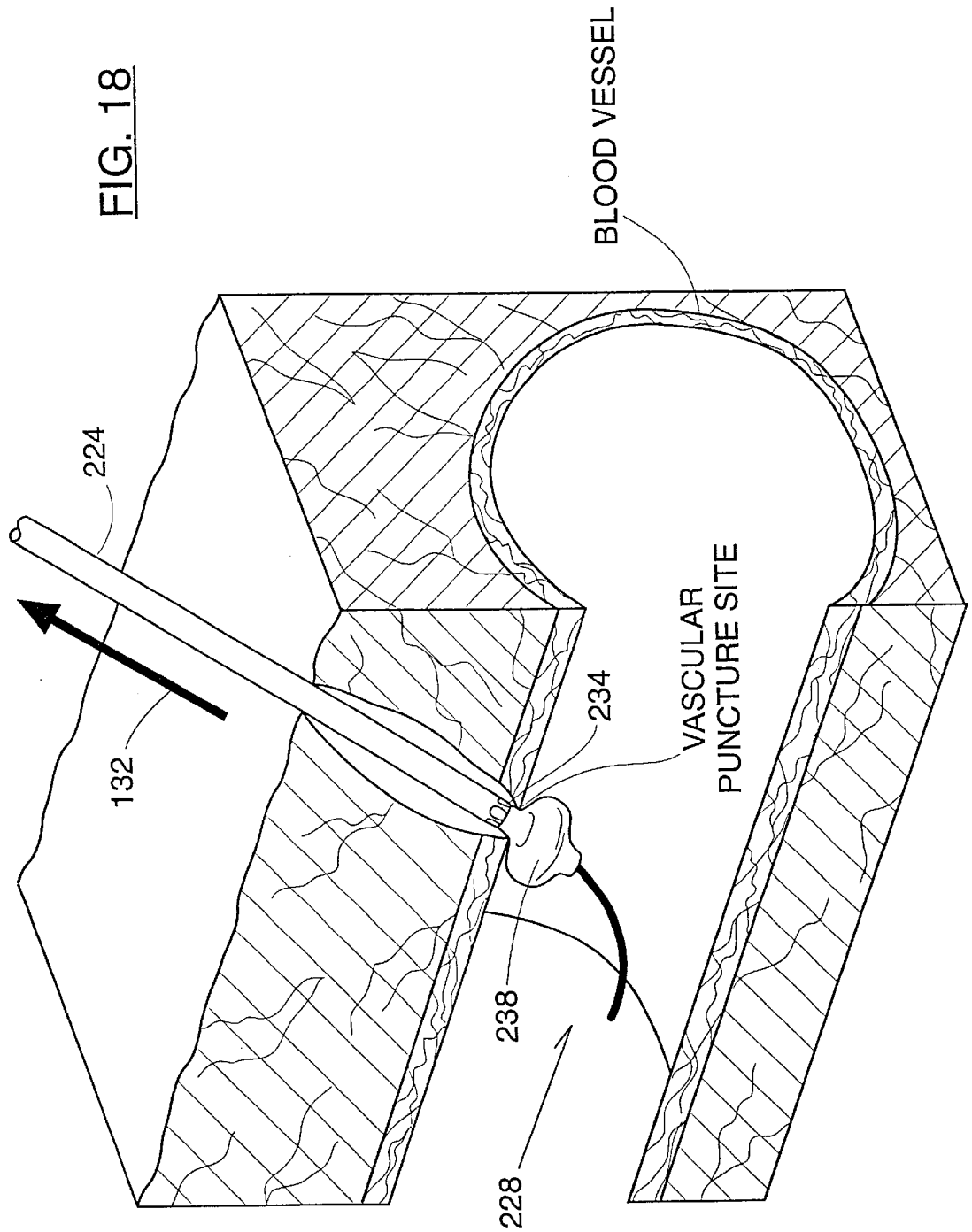
FIG. 18 is a schematic perspective view of the distal end of the catheter device shown in FIG. 17, when expanded for use at the vascular puncture site.

According to the directions 122 (as FIG. 18 shows), the physician is instructed to attach an auxiliary syringe 126 filled with about 1 cc of air to the fitting 254. The phsyician injects the air to inflate the region 238, which expands radially into the positioner 242. The physician is then instructed to place slight rearward tension on the catheter tube 224 (shown by arrow 132 in FIG. 18), to bring the positioner 242 into contact with the interior of the vessel. Due to the slight rearward tension, the positioner 242 seats against and supports the puncture site. The physician will, by tactile feedback, know that the positioner 42 has contacted the vessel interior. The guidewire lumen 32 of the catheter tube 24 can be used to inject suitable contrast media to aid in the visualization of the puncture site region.

The physician is instructed to continue to apply a slight rearward tension on the catheter tube 224, sufficient to keep the positioner 242 against the interior of the vessel, without pulling it through the vessel wall.

The physician is instructed to grasp the finger rests 80 and thumb rest 82 of the barrier material introducer/mixer 22, as if grasping an ordinary syringe. The physician expresses the albumin 100 from the first dispensing syringe 60 while simultaneously also expressing the PEG solution 136 from the second dispensing syringe 62.

The albumin and PEG solutions come into contact in the mixing chamber 294 and, from there, proceed through the catheter tube 224 to the nozzles 234. The albumin 100 and PEG solution 136 intimately channel-mix in transit.

Figure 19:
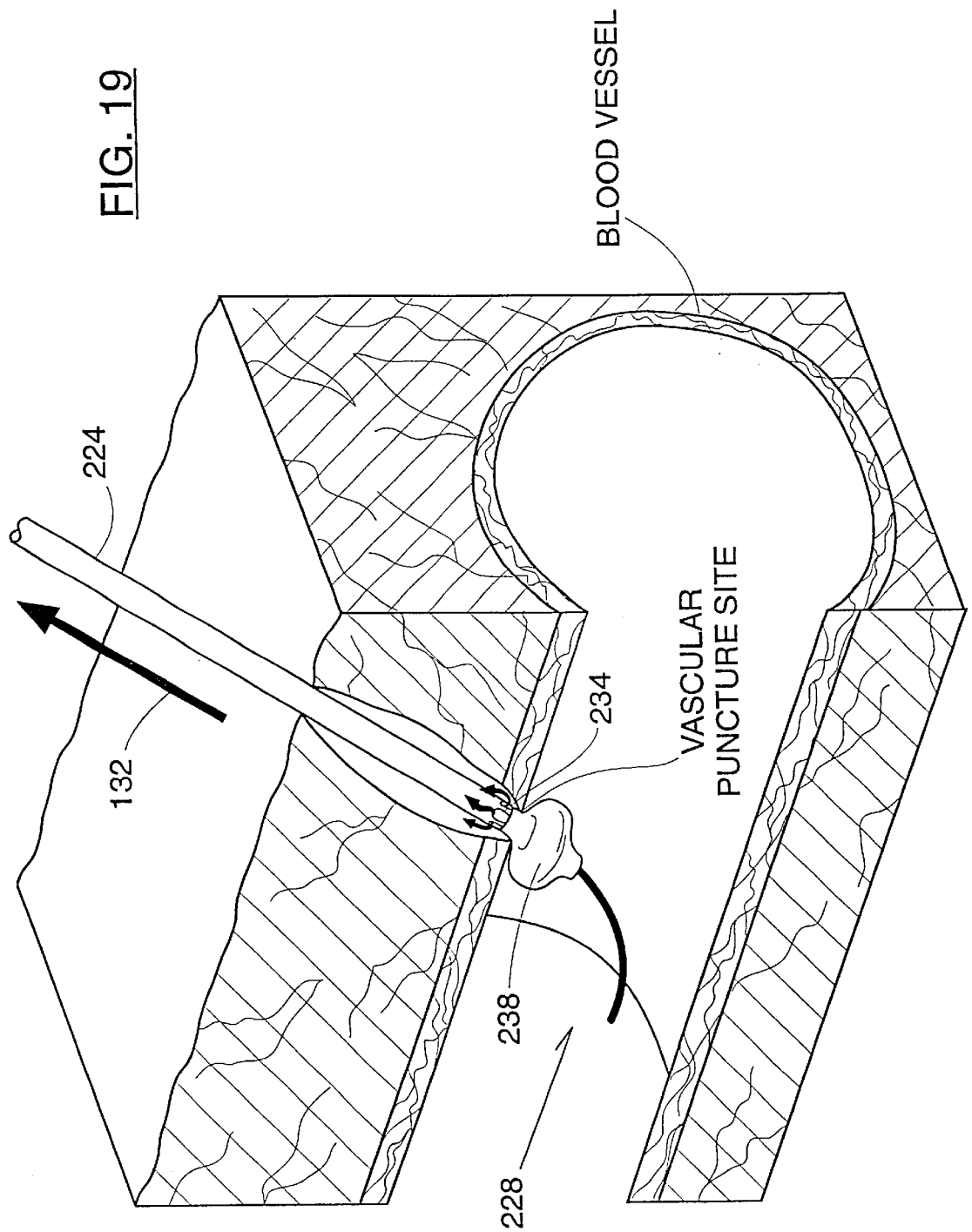
FIG. 19 is a schematic perspective view of the distal end of the catheter device shown in FIG. 18, as barrier material is dispensed in liquid form in tissue outside the vascular puncture site.

As FIG. 19 shows, the mixture of albumin 100 and PEG solution 136 flows in liquid form through the nozzles 234. The liquid mixture 130 of albumin 100 and PEG solution 136 enters and fills the tissue region surrounding the puncture site.

As FIG. 19 shows, according to the directions 122, the physician waits the requisite gelation period, during which the liquid mixture 130 of albumin 100 and PEG material 136 transform into a non-fluid barrier network 128 outside the puncture site. During the gelation period, the physician is instructed to continue to apply a slight rearward tension on the catheter tube 224 to seat the positioner 242 against the interior vessel wall, as the solid barrier network 128 forms outside the vessel to seal the puncture site. The catheter tube 224 resists seepage of the liquid mixture 130 into the vessel during the gelation period.

Figure 20:
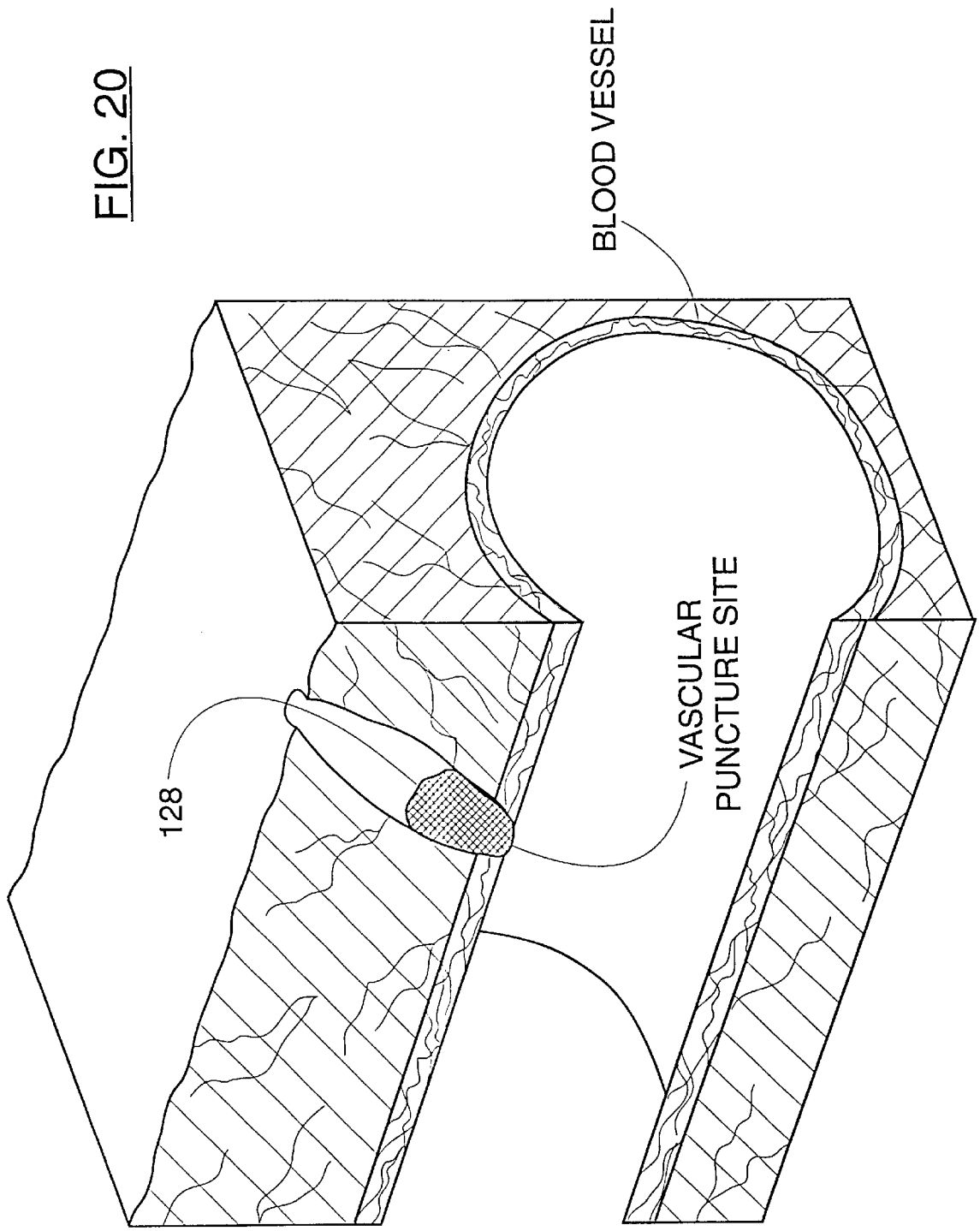
FIG. 20 is the non-liquid barrier network formed after the liquid barrier material cross-links in situ in tissue to seal the vascular puncture site.

After the requisite gelation period, the physician is instructed to operate the syringe 126 to remove air pressure and collapse the positioner 242. The physician withdraws the guide wire 40 and the distal end 228 of the catheter tube 24 from the vessel. As shown by FIG. 20, during withdrawal, the distal end 28 and the guide wire 40 pass through the barrier network 128 that has, by now, formed over the puncture site.

After withdrawing the catheter tube 24, the physician is instructed to apply manual pressure to the skin over the blood vessel, e.g., for about three minutes, to aid in the sealing process. This time allows the barrier material to fully cross-link. The physician then confirms that the puncture site has been sealed by observing the lack of blood seepage about the guide wire access.

The puncture site of the vessel naturally closes and heals. As FIG. 20 shows, the presence of the barrier network 128 outside the puncture site prevents blood leakage while natural healing takes place. The body resorbs the barrier network 128 over time, e.g., within 30 days.

C. Mixing Chambers

There are various alternative constructions for a mixing chamber 94 usable in association with the barrier material introducer/mixer 22. The construction selected depends upon the particular geometry and size of a given mixing chamber, as well as how readily the components of the barrier material intimately mix to initiate the cross-linking reaction.

In the illustrated embodiment, the enhanced functionality of the preferred 4-PEG-SG material allows channel mixing to take place, as the components of the barrier are conveyed in tandem to the targeted puncture site. In this arrangement, the mixing chamber 94 serves the function of rapidly guiding the polymer solution 136 and the protein solution 100 into intimate flow contact as they leave the port 92.

The mixing chamber 94 can, if desired, include other structure to mechanically enhance and accelerate the mixing effect.

Figure 22:
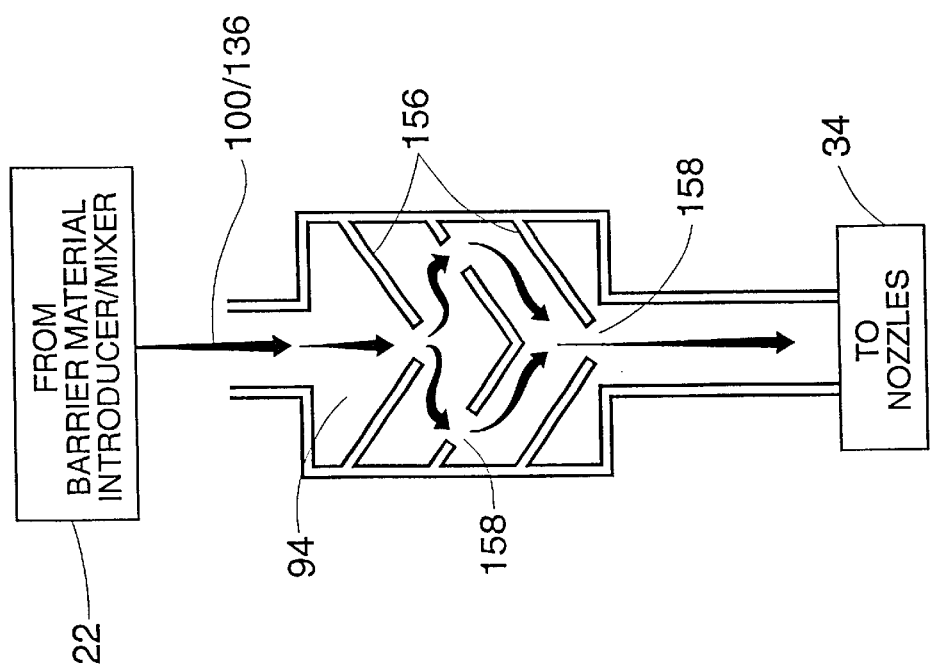
FIG. 22 is an enlarged sectional view showing the interior of a mixing chamber usable in association with the barrier material introducer shown in FIG. 9, the interior containing an array of baffle funnels with staggered interruptions to establish a circular flow path through the chamber for the purpose of accelerating mixing of the liquid components of the barrier material.

For example, as shown in FIG. 22, a mixing chamber 94 can include an array of interior funnel walls 156. The funnel walls 156 include interruptions 158, which are arranged in a alternative pattern along the flow center and along the flow perimeter of the chamber 154. Polymer solution 136 and protein solution 100 are directed through the interruptions 158 in a circumferential and circular flow path through the chamber 154. The circumferential and circular flow of the polymer solution 136 and protein solution 100 accelerates the channel-mixing process.

Figure 23:
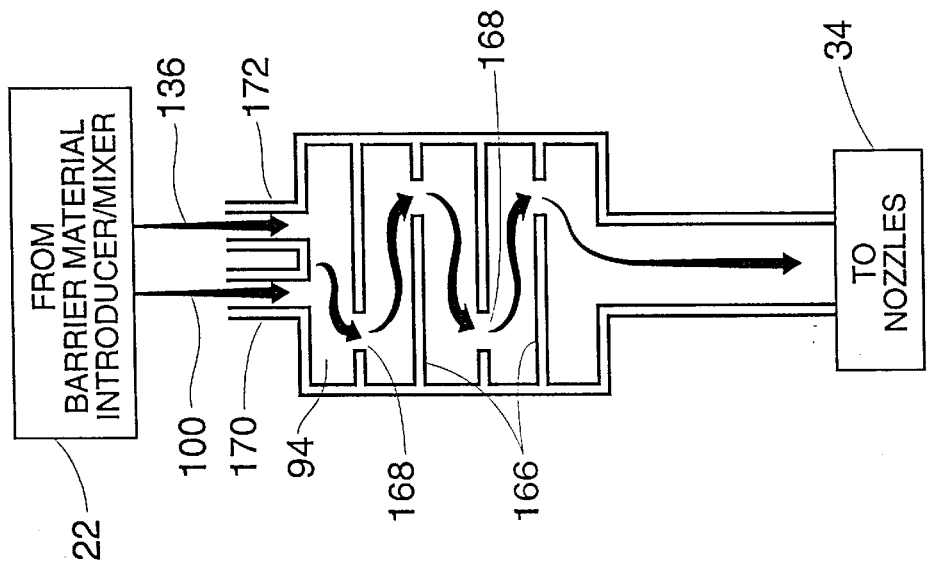
FIG. 23 is an enlarged sectional view showing the interior of a mixing chamber usable in association with the barrier material introducer shown in FIG. 9, the interior containing an array of baffle walls with staggered interruptions to establish a zig-zagging flow path through the chamber for the purpose of accelerating mixing of the liquid components of the barrier material.

Alternatively (as FIG. 23 shows), baffle walls 166 can be arranged perpendicular to the flow path through the mixing chamber 94. The baffle walls 166 include staggered interruptions 168. The interruptions 168 cause the polymer solution 136 and protein solution 100 to advance through the chamber 94 in a zig-zagging path, from one side of the chamber 94 to the other. The zig-zagging path is particularly advantageous if the polymer solution 136 and protein solution 100 are introduced into the chamber 94 through separate inlet ports 170 and 172).

Figure 25:
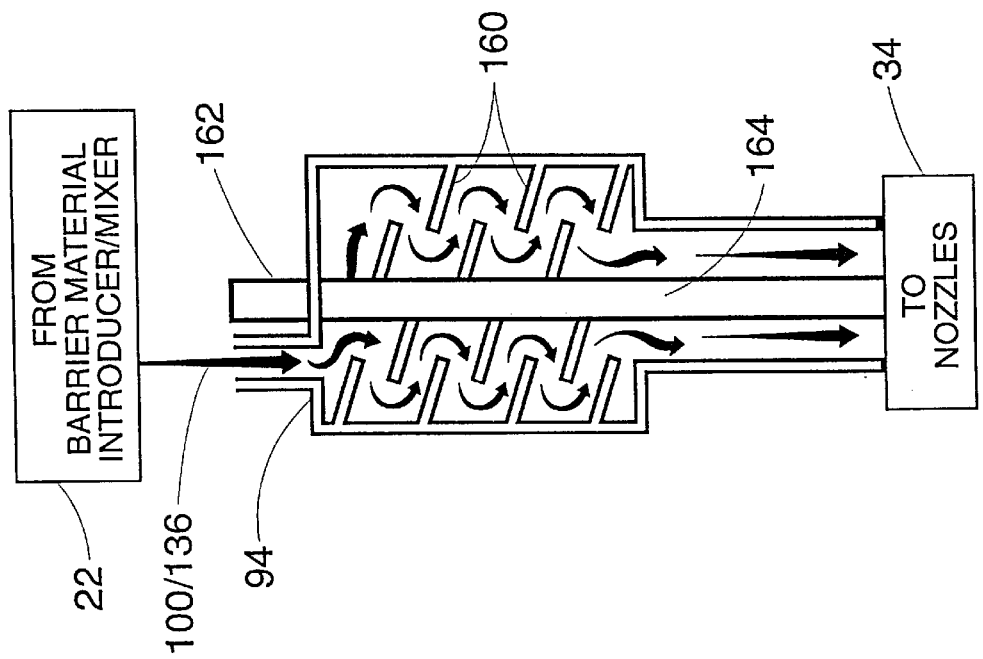
FIG. 25 is an enlarged sectional view showing the interior of a mixing chamber usable in association with the barrier material introducer shown in FIG. 9, the interior containing an array of staggered baffle walls to establish a cascading flow path through the chamber for the purpose of accelerating mixing of the liquid components of the barrier material.
Figure 24:
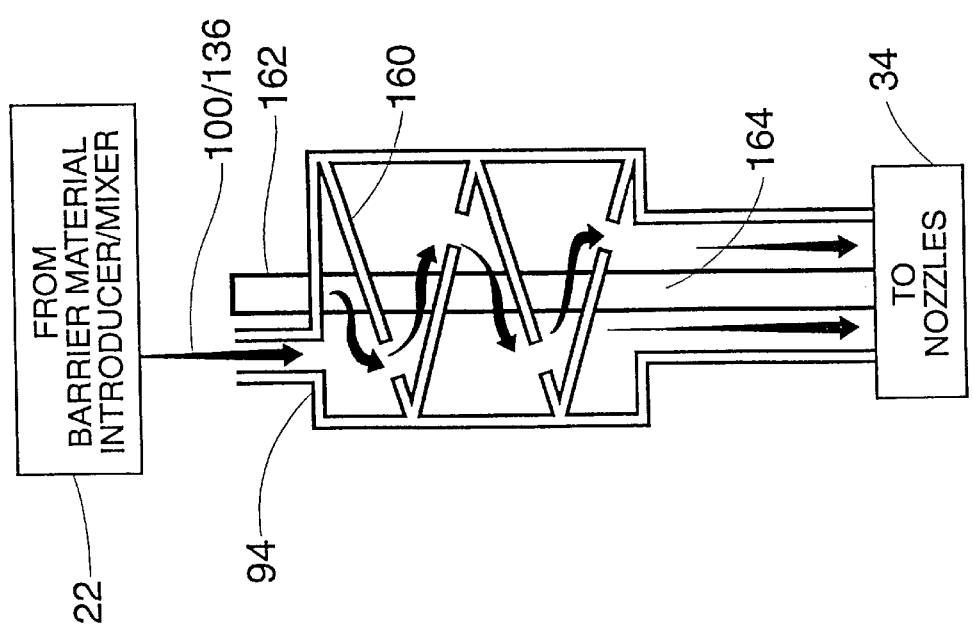
FIG. 24 is an enlarged sectional view showing the interior of a mixing chamber usable in association with the barrier material introducer shown in FIG. 9, the interior containing a spiral baffle to establish a circular flow path through the chamber for the purpose of accelerating mixing of the liquid components of the barrier material.

Alternatively, baffles 160 can be arranged about a hub 162 in a spiral pattern (as FIG. 24 shows) or in a non-spiral pattern (as FIG. 25 shows). The baffles 160 establish a cascading flow within the chamber 94 to accelerate mixing of the polymer solution 136 and protein solution 100. The hub 162 can include an interior lumen 164 to accommodate passage of, e.g., the guide wire 40 or the air conveyed to expand a deformable region on the distal end of the catheter tube 24 or 224.

As FIG. 26 shows, the polymer solution 136 and the protein solution 100 can be introduced into the chamber 94 through separate tangential ports 174 and 176, which are diagonally spaced apart. The chamber 94 includes a center outlet port 178. Solutions 100 and 136 entering the ports 174 and 176 flow in a swirling pattern about the periphery of the chamber 94, before exiting the center outlet port 178. The swirling flow pattern accelerates intimate mixing.

As shown in FIG. 27, the chamber 94 can include multiple spaced apart inlet ports 180, 182, 184, 186 arranged about a common center outlet port 188. The ports 180, 182, 184, 186, and 188 are arranged parallel to the intended flow path through the chamber 94. Polymer solution 136 is introduced through opposed ports 180 and 184, while protein solution is introduced through the opposed ports 182 and 186. The multiple spaced-apart inlet paths feeding a common center outlet port 188 enhance the desired mixing effect of the chamber 94.

C. Other Uses for the Barrier Material Introducer/Mixer

Figure 21:
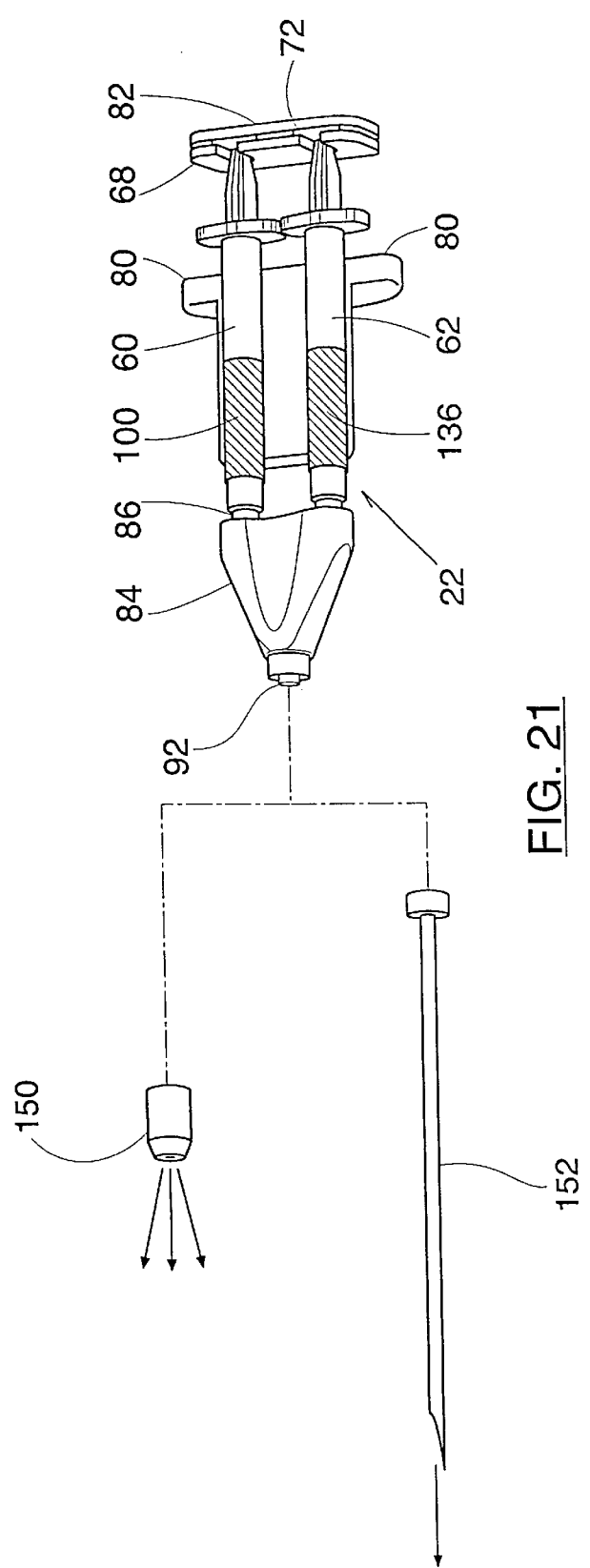
FIG. 21 is a perspective view of the barrier material introducer/mixer shown in FIG. 9 when used in association with a sprayer or a cannula, to dispense barrier material without use of a catheter device.

The barrier material introducer/mixer 22 can be used to dispense barrier material without association with the catheter device 20 or 220. As FIG. 21, the outlet port 92 can be coupled to various dispensing devices, such as a sprayer 150 or a cannula or needle 152.

The physician can select the sprayer 150 and operate the material introducer/mixer 22 in the manner previously described, to locally dispense the barrier material (or an other tissue adhesive or sealing material) at an exposed puncture or suture site, e.g., during an open surgical procedure or on the skin. Atomization through the sprayer 150 will mix the liquid components of the barrier or adhesive material sufficiently to initiate the cross-linking reaction.

Alternatively, the physician can select the cannula 152 and operate the material introducer/mixer 22 to inject the barrier material (or other selected material) at a targeted subcutaneous puncture site. Passage of the liquid components of the barrier or other material through the cannula 152 will channel-mix the materials sufficiently to initiate the cross-linking reaction.

It should thus be appreciated that the barrier material introducer/mixer 22 can be used in diverse ways throughout the body for dispensing any material formed by intimate mixing of two liquid components conveyed in tandem to a targeted treatment site. The barrier material introducer/mixer 22 can be used for exterior or interior introduction and application of any such material, with or without catheter access.

D. Introducer/Mixer

Figure 28:
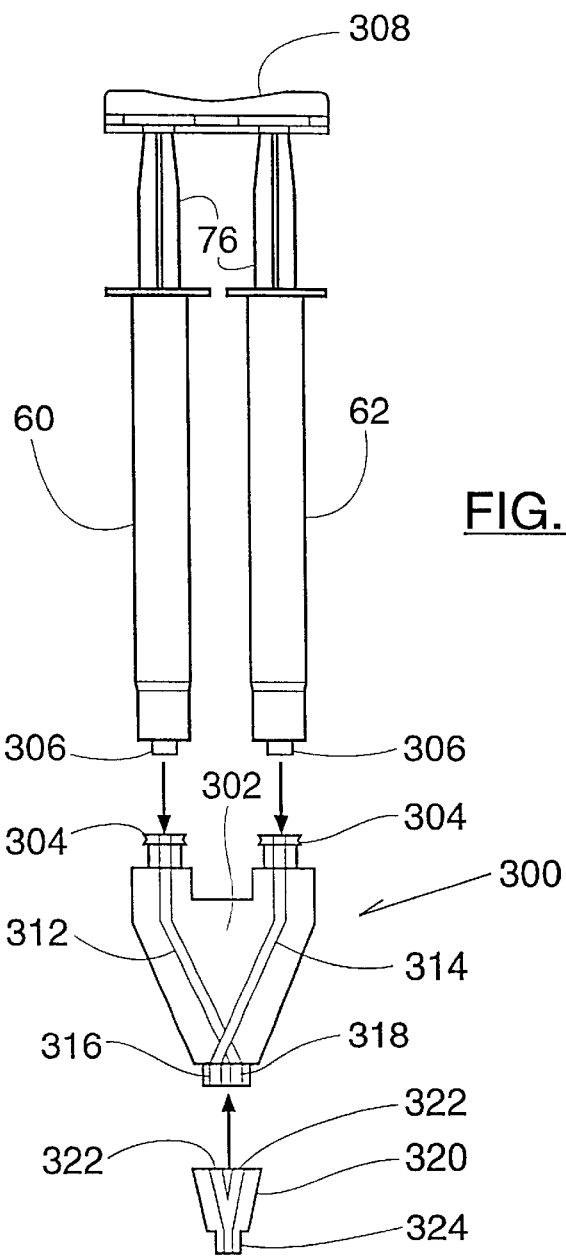
FIG. 28 is a side elevation view of an alternative embodiment of an introducer/mixer, which can be used in association with the system shown in FIG. 1.

FIG. 28 shows an alternative embodiment of an introducer/mixer 300. In this embodiment, a molded joiner 320 includes side-by-side female luer fittings 304. Each fitting 304 receives the threaded male luer fittings 306 of the dispensing syringes 60 and 62. A syringe clip 308 also preferably links the syringe pistons 76 for simultaneous advancement when dispensing materials from the syringes 60 and 62.

In this alternative embodiment, the introducer/mixer 300 does not include a separate channeled syringe support member (as shown by reference numeral 34 in FIG. 2). The molded strength of the female luer fittings 304 on the joiner 302, can, when threaded to the male fittings 306, itself be sufficient to hold the syringes 60 and 62 during dispensement of their liquid contents, as already described. This reduces the number of parts required for the introducer/mixer 300.

Figure 29:
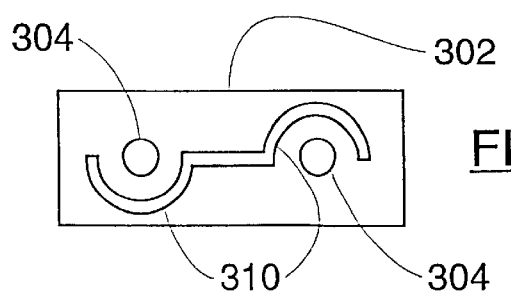
FIG. 29 is a top view of an alternative embodiment of an introducer/mixer of the type shown in FIG. 28, showing the presence of skirts to resist side-to-side deflection of syringes en; supported by the introducer/mixer.

As FIG. 29 shows, the joiner 302 can include opposing skirts 310 molded to peripherally surround the fittings 304. The skirts 310 resist side-to-side deflection of the syringes 60 and 62, when held by the joiner 302.

As FIG. 28 shows, the joiner 302 includes interior channels 312 and 314, which are coupled to the luer fittings 304.

The interior channels 312 and 314 criss-cross within the joiner 302, without fluid communication. The criss-crossing channels 312 and 314 keep the liquid contents of the syringes 60 and 62 free of mixing. The channels 312 terminate with separate outlet ports 316 and 318.

As FIG. 28 also shows, in use, the joiner 302 is coupled to a mixing chamber 320, which is of the type shown in FIG. 27. The liquid contents of the syringes 60 and 62 are transported through the outlet ports 316 and 318 from the joiner 302 into separate, spaced-apart ports 322 in the mixing chamber 320. The ports 322 lead to a common center outlet port 324. As before explained, the flow of the liquid contents through separate spaced-apart inlet ports 322 into a common outlet port 324 enhances the mixing effects of the chamber 320.

Figure 30:
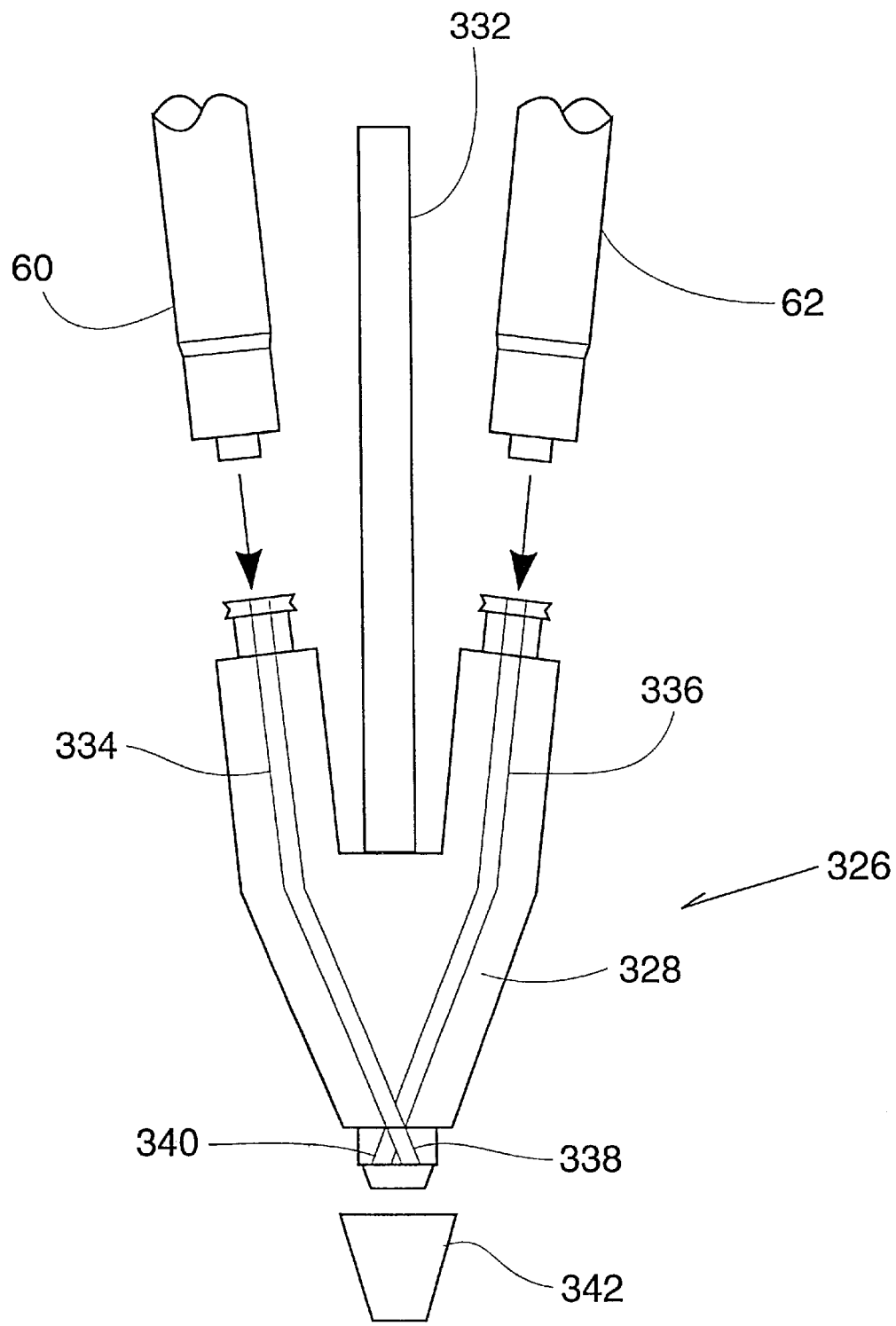
FIG. 30 is a side elevation view of an other alternative embodiment of an introducer/mixer, which can be used in association with the system shown in FIG. 1.

FIG. 30 shows yet another alternative embodiment of an introducer/mixer 326. In this embodiment, a molded joiner 328 includes female luer fittings 330, to receive the threaded male luer fittings 306 of the dispensing syringes 60 and 62. In this embodiment, the fittings 330 extend in a generally v-shape, at an angle and not parallel with respect to each. This allows the main body of the joiner 328 to be reduced in size. A syringe clip (not shown) can be used to link the syringe pistons coupled to the joiner 328 for simultaneous advancement.

In this alternative embodiment, the introducer/mixer 326 also does not include a separate channeled syringe support member (as shown by reference numeral 34 in FIG. 2). The molded strength of the female luer fittings 330 itself can be sufficient to support the syringes 60 and 62 during use. As FIG. 30 shows, an intermediate wall 332 can be provided between the fittings 330 to resist inward deflection of the syringes 60 and 62 during use.

As FIG. 30 shows, the joiner 328 includes criss-crossing interior channels 334 and 336, like those shown in FIG. 28. The channels 334 and 336 terminate with separate outlet ports 338 and 340, which, in use, are coupled to a mixing chamber 342 of the type shown in FIG. 28 and previously described.

Of course, the joiners 302 and 328 can be coupled to other types of mixing chambers.

The features of the invention are set forth in the following claims.

We claim:

1. A biocompatible and biodegradable material applied to seal a vascular puncture comprising a mixture of buffered protein solution having a pH value of between about 7 and about 10 and comprising recombinant or natural human serum albumin at a concentration of about 25% or less, and a polymer solution comprising poly(ethylene glycol)(PEG) with a functionality of at least three, wherein, upon mixing, the buffered protein solution and the polymer solution cross-link to form a solid matrix that seals the vascular puncture without use of a photo-initiator and ultraviolet light energy.

2. A material according to claim 1, wherein the buffered protein solution has a pH value of between about 8 and about 10.

3. A material according to claim 1, wherein the PEG has a molecular weight of between about 10,000 and 15,000 g/mole.

4. A material according to claim 1, wherein the PEG comprises a multi-armed polymer structure.

5. A material according to claim 1, wherein PEG comprises a compound having the formula PEG–(DCR–CG)n, where PEG is poly(ethylene glycol), DCR is a degradation control region, CG is a cross-linking group, and n is equal to or greater than three.

6. A material according to claim 5, wherein the compound comprises a multi-armed polymer structure.

7. A material according to claim 5, wherein the PEG comprises a 4-arm PEG, the degradation control region comprises glutaric acid, and the cross-linking group includes a N-hydroxysuccinimide ester.

8. A material according to claim 1, wherein the PEG has a functionality of four.

9. A material according to claim 1, wherein the PEG has a concentration that ranges from about 5% to about 35% w/w.

* * * * *